US011666468B2

(12) United States Patent
Sander et al.

(10) Patent No.: US 11,666,468 B2
(45) Date of Patent: Jun. 6, 2023

(54) DUODENAL GASTROINTESTINAL DEVICES AND DELIVERY MECHANISMS

(71) Applicant: ENDOSPHERE, INC., Columbus, OH (US)

(72) Inventors: Fiona M. Sander, Los Altos Hills, CA (US); John P. Lunsford, San Carlos, CA (US); Stacy Patch, San Jose, CA (US); Adrian Borlan, Dresden (DE)

(73) Assignee: Endosphere, Inc., Columbus, OH (US)

( * ) Notice: Subject to any disclaimer, the term of this patent is extended or adjusted under 35 U.S.C. 154(b) by 343 days.

(21) Appl. No.: 15/318,441

(22) PCT Filed: Jun. 19, 2015

(86) PCT No.: PCT/US2015/036812
§ 371 (c)(1),
(2) Date: Dec. 13, 2016

(87) PCT Pub. No.: WO2015/196157
PCT Pub. Date: Dec. 23, 2015

(65) Prior Publication Data
US 2017/0128247 A1 May 11, 2017

Related U.S. Application Data

(60) Provisional application No. 62/014,613, filed on Jun. 19, 2014.

(51) Int. Cl.
*A61F 5/00* (2006.01)

(52) U.S. Cl.
CPC .......... *A61F 5/0076* (2013.01); *A61F 5/0089* (2013.01)

(58) Field of Classification Search
CPC ...... A61F 5/0076; A61F 5/0089; A61F 5/003; A61F 5/0013; A61F 5/0079
See application file for complete search history.

(56) References Cited

U.S. PATENT DOCUMENTS

| | | | | |
|---|---|---|---|---|
| 2010/0010293 A1* | 1/2010 | Sato | ...................... | A61B 1/0014 600/101 |
| 2011/0270405 A1* | 11/2011 | Geitz | .................... | A61F 5/0076 140/3 R |
| 2013/0331759 A1* | 12/2013 | Neisz | ................... | A61F 5/0076 604/8 |

* cited by examiner

*Primary Examiner* — Brooke Labranche
(74) *Attorney, Agent, or Firm* — Erickson Law Group, PC

(57) ABSTRACT

A system for delivering an endolumenal device through an endoscope includes a delivery tool and an adaptor. The delivery tool has an elongate tube configured to hold a portion of the endolumenal device therein and a first connecting feature on a distal end of the elongate tube. The adaptor is configured to attach to a handle of the endoscope. The adaptor includes a channel therethrough and a second connecting feature configured to mate with the first connecting feature of the delivery tool. The elongate tube of the delivery tool is configured to align with the channel of the adaptor when the first and second connecting features are mated.

16 Claims, 55 Drawing Sheets

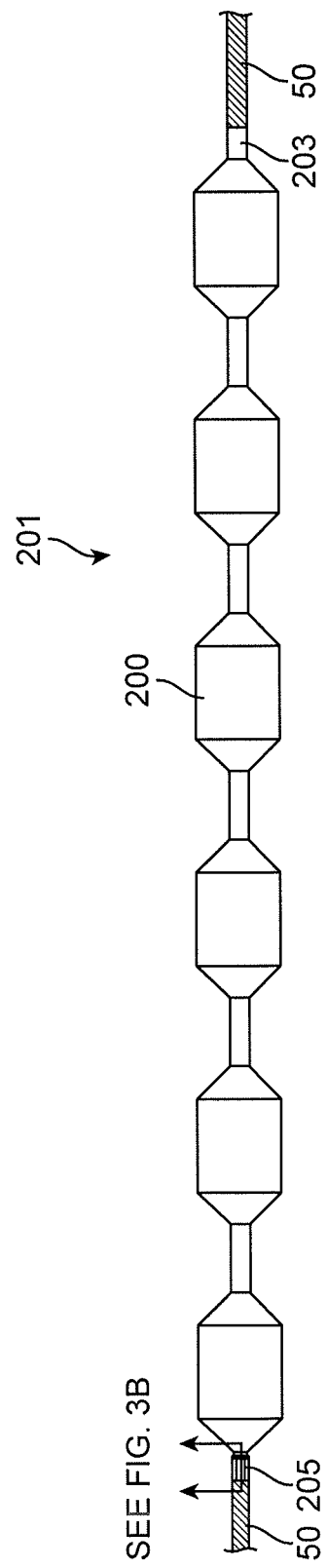
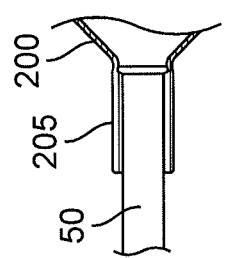

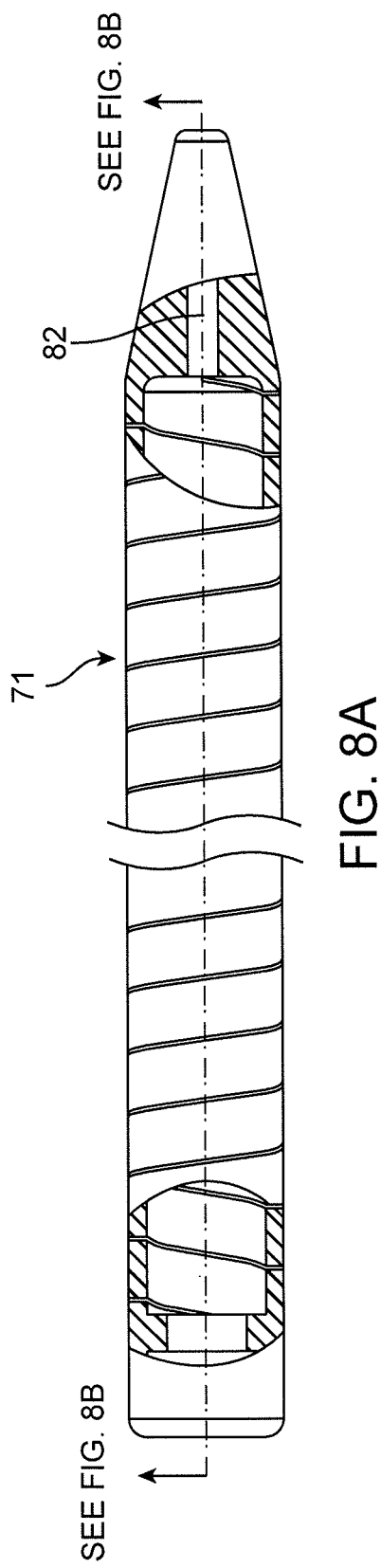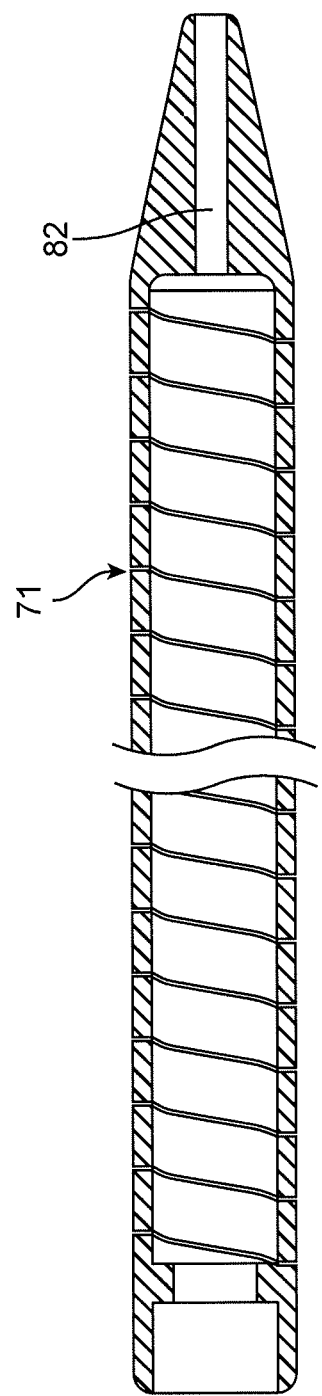
FIG. 8A
FIG. 8B

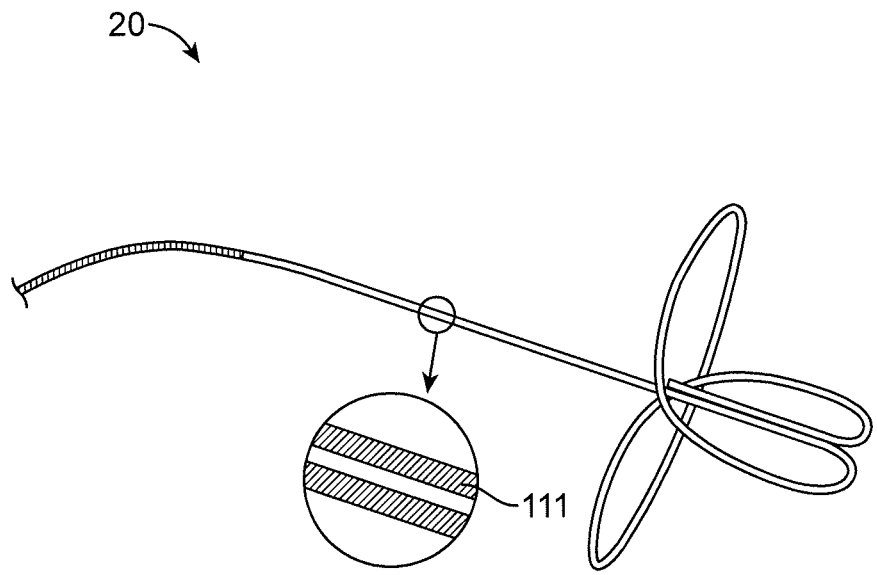
FIG. 10A
FIG. 10B
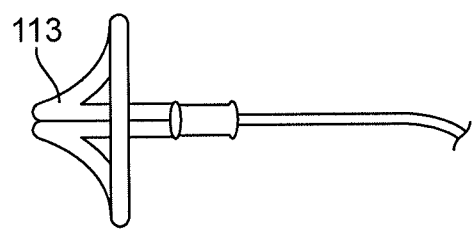
FIG. 10C

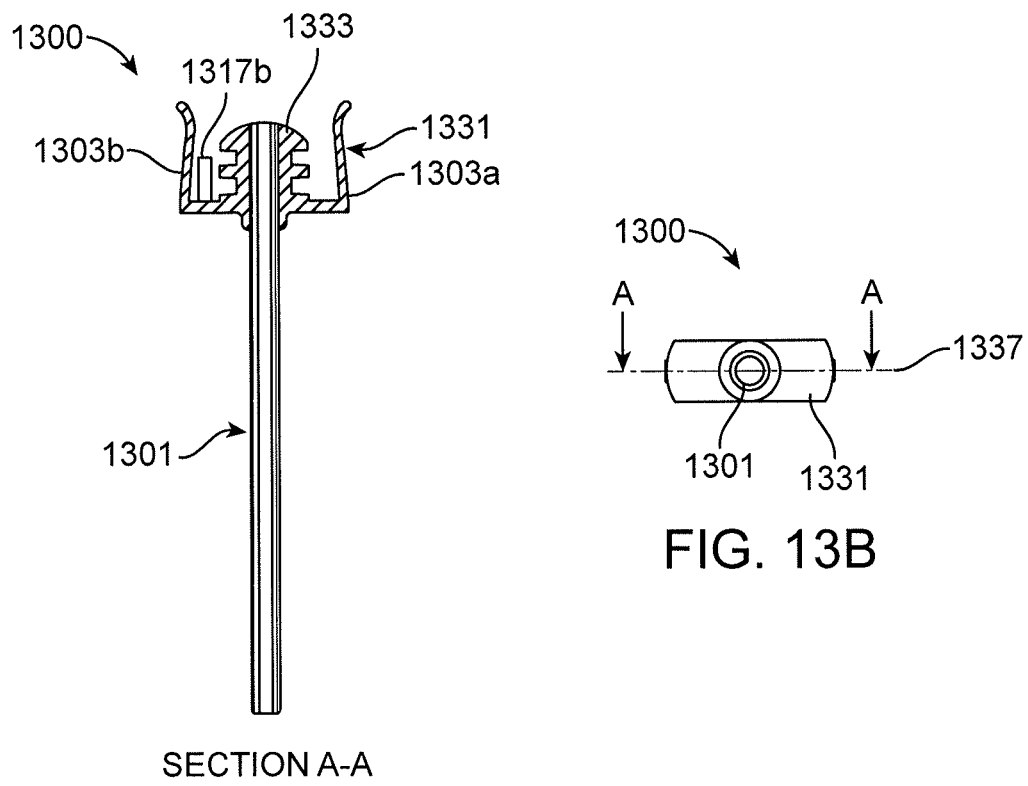
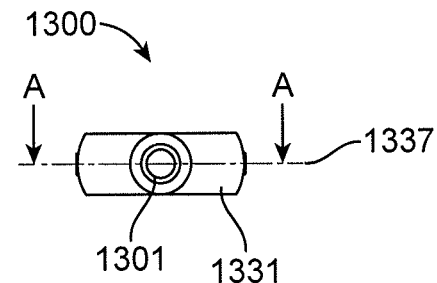
SECTION A-A
FIG. 13A
FIG. 13B
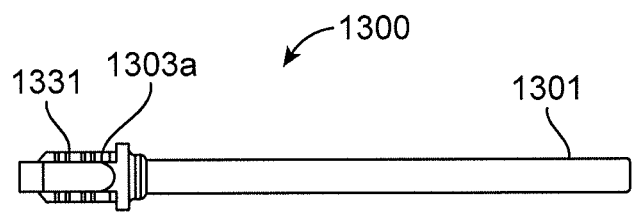
FIG. 13C
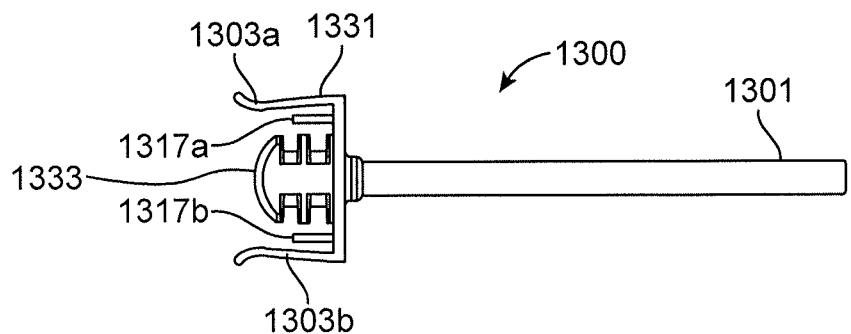
FIG. 13D

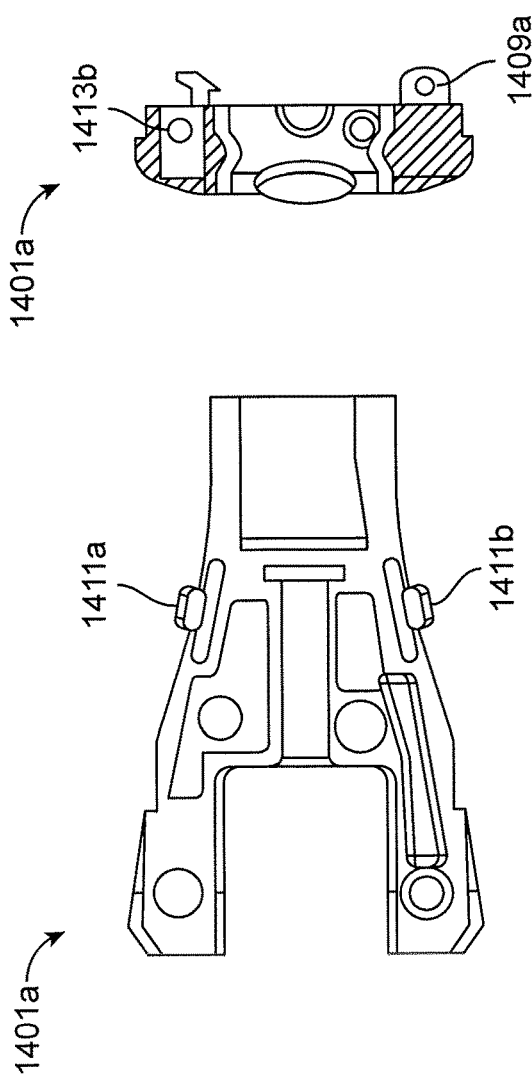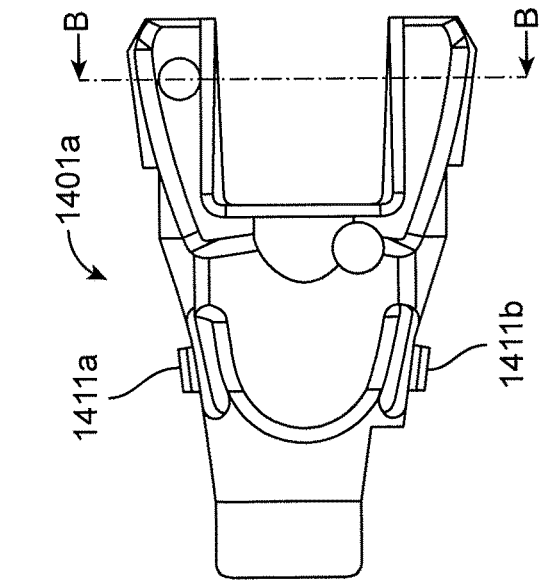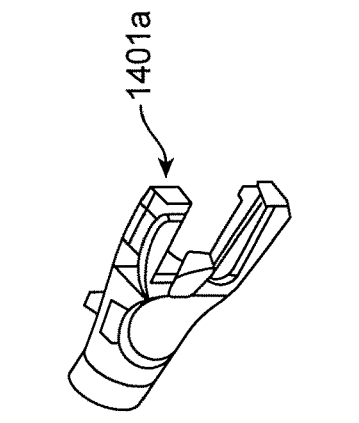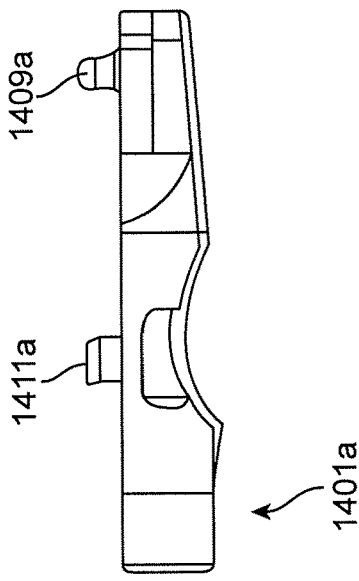

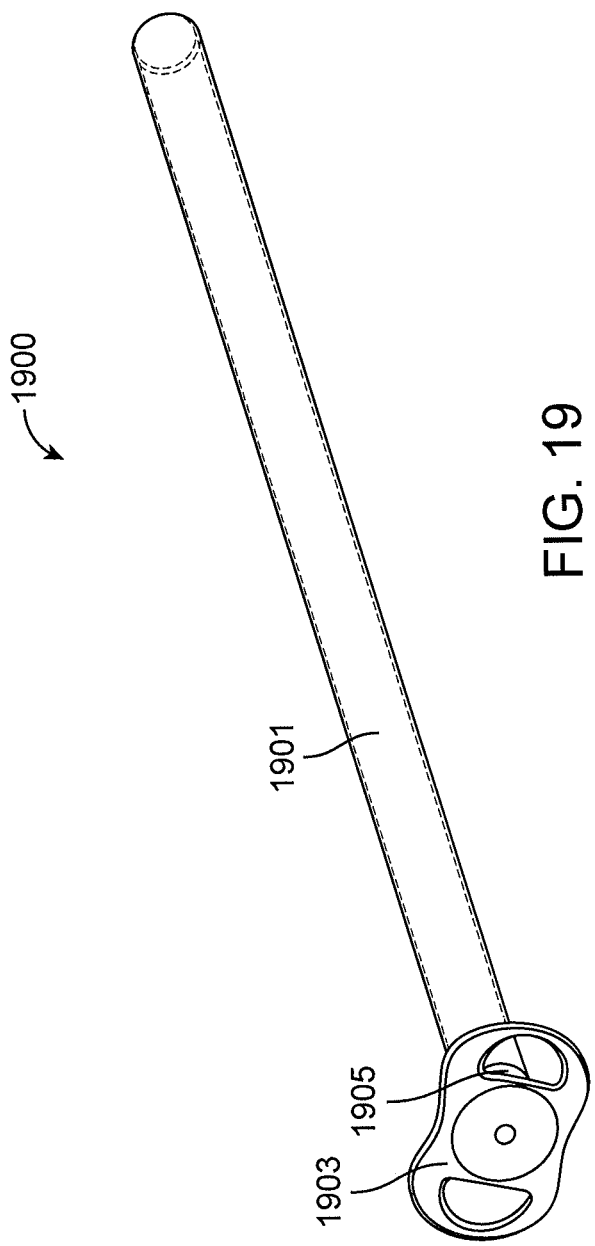

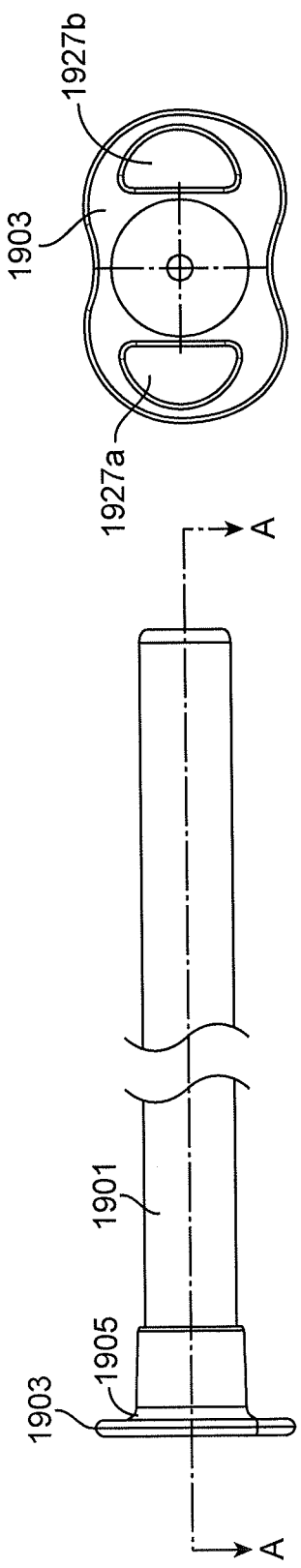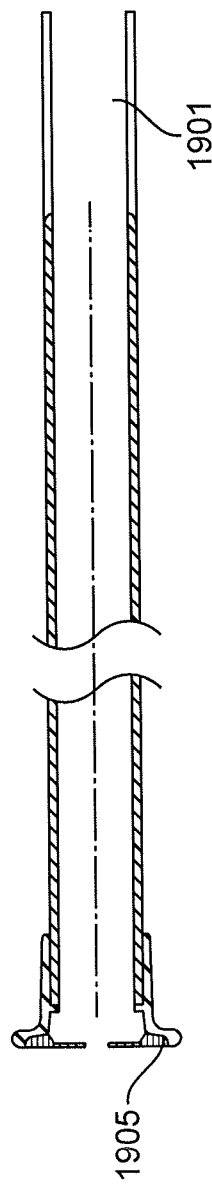
FIG. 20B
FIG. 20A
FIG. 20C
SECTION A-A

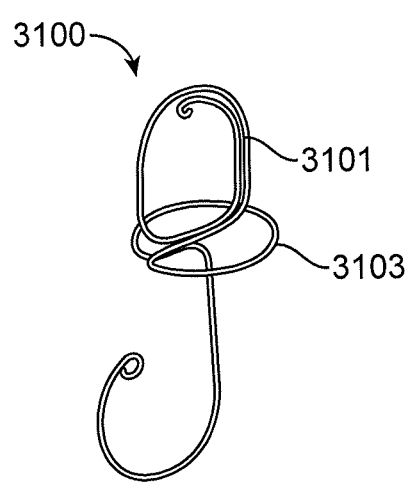
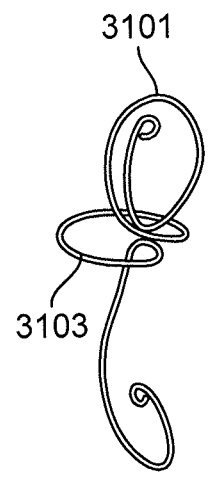
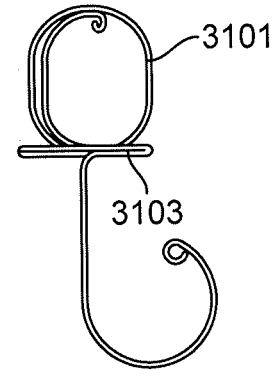
FIG. 31A        FIG. 31B        FIG. 31C
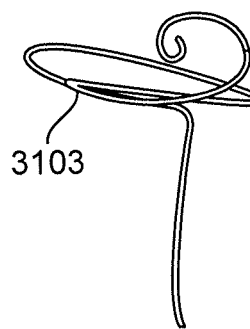
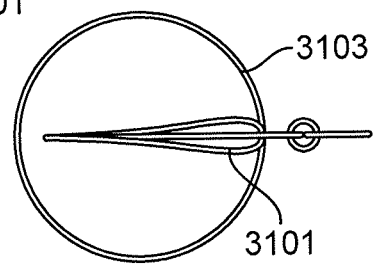
FIG. 31D        FIG. 31E

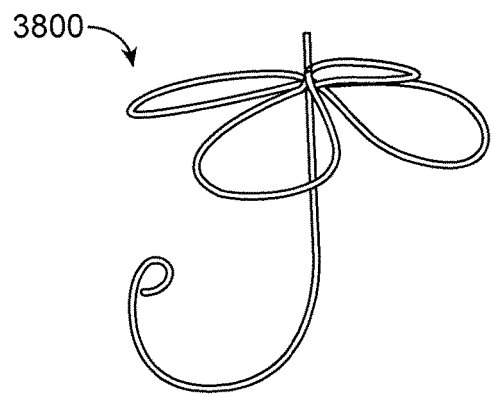 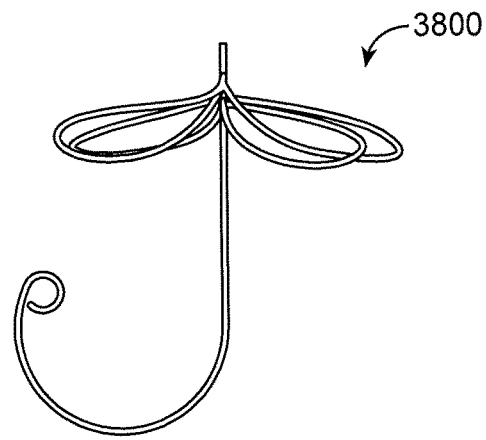
FIG. 38A　　　　　　　　　　　FIG. 38B
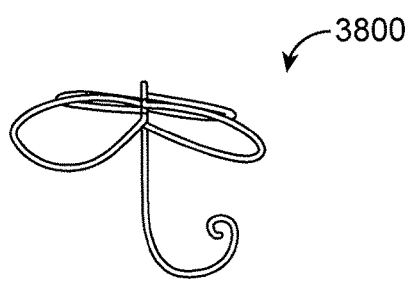 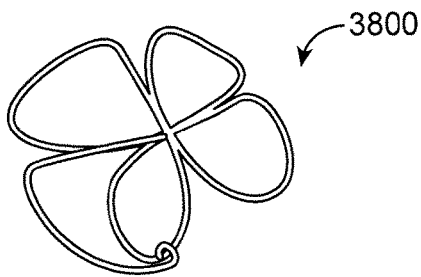
FIG. 38C　　　　　　　　　　　FIG. 38D
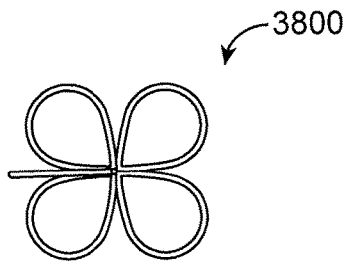
FIG. 38E

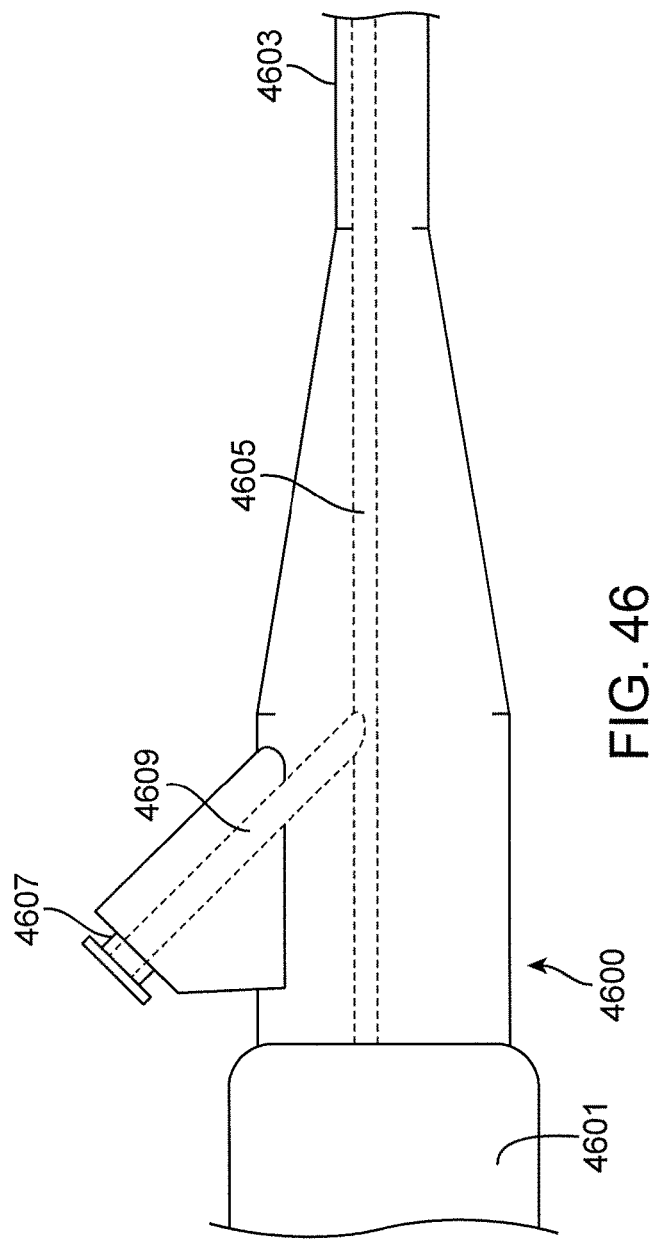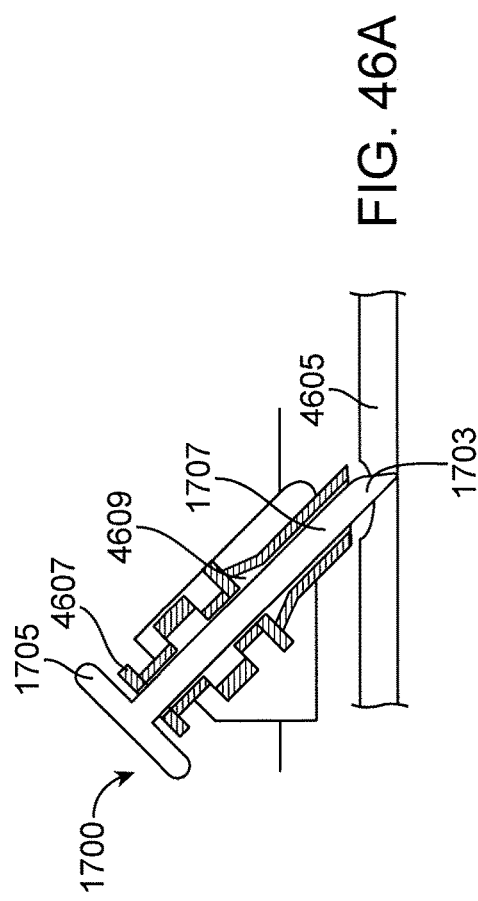

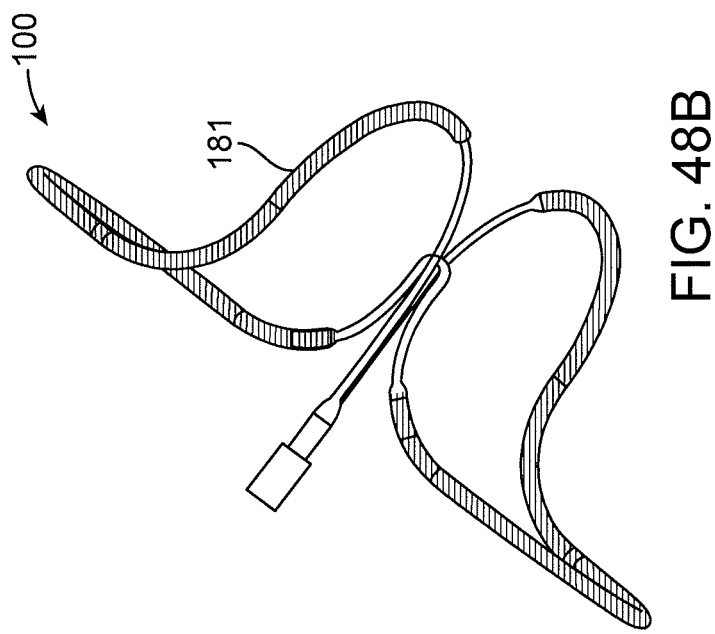
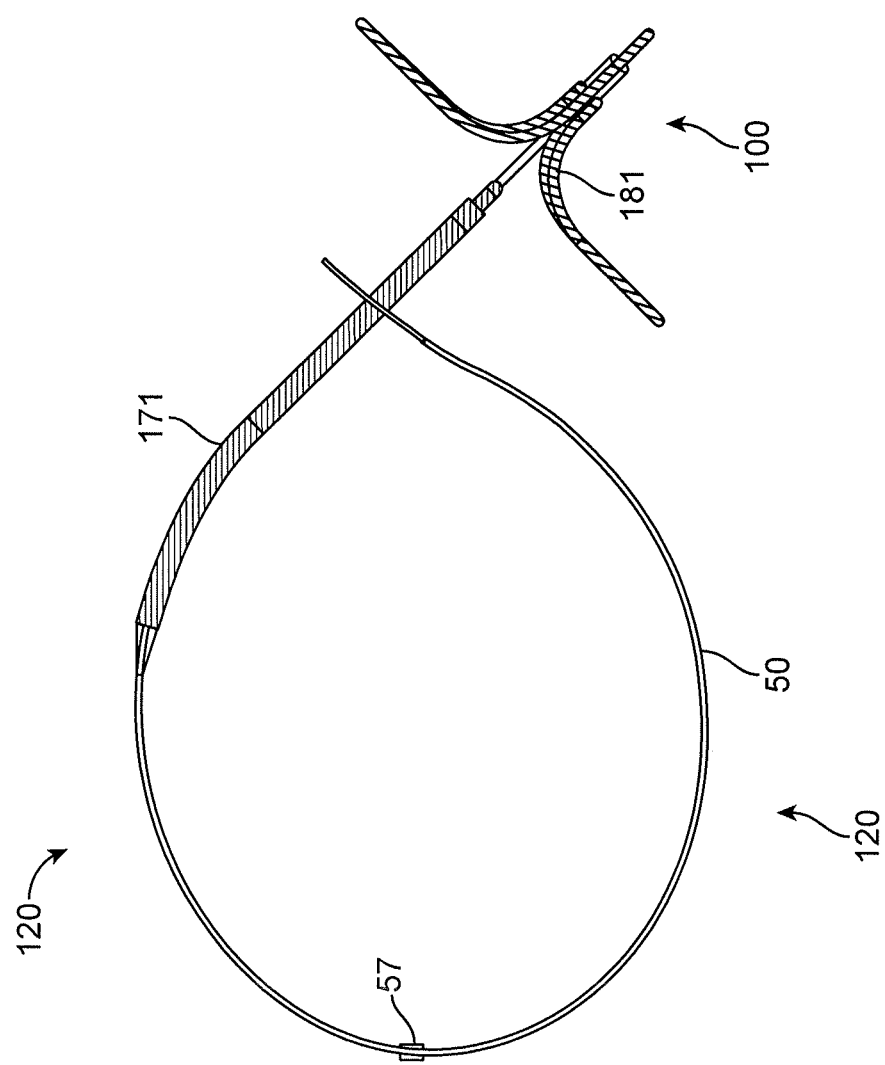
FIG. 48A
FIG. 48B

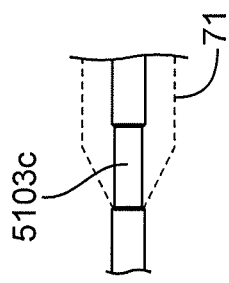
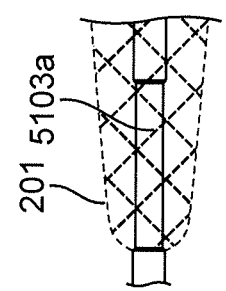
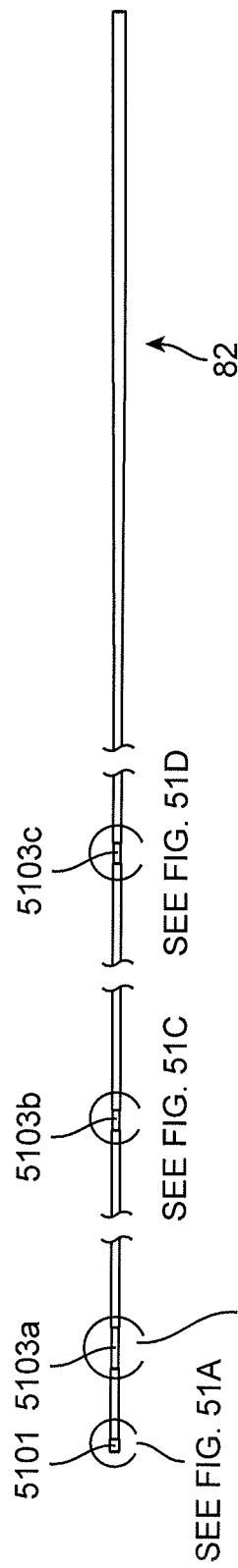

DUODENAL GASTROINTESTINAL DEVICES AND DELIVERY MECHANISMS

CROSS REFERENCE TO RELATED APPLICATIONS

This patent application claims priority to U.S. Provisional Patent Application No. 62/014,613, titled "DUODENAL GASTROINTESTINAL DEVICES AND DELIVERY MECHANISMS," filed Jun. 19, 2014, which is herein incorporated by reference in its entirety.

This application may be related to U.S. patent application Ser. No. 13/666,919, filed Nov. 1, 2012, titled "DUODENAL GASTROINTESTINAL DEVICES AND RELATED TREATMENT METHODS," now U.S. Patent Application Publication No. 2013-0109912-A1, the entirety of which is incorporated by reference herein.

INCORPORATION BY REFERENCE

All publications, patents and patent applications mentioned in this specification are herein incorporated by reference to the same extent as if each individual publication, patent or patent application was specifically and individually indicated to be incorporated by reference.

FIELD

The invention is in the field of medical devices that reside within a lumen of the gastrointestinal tract. More particularly, the devices described herein stabilize within the small intestine.

BACKGROUND

Obesity, defined as a body mass index (BMI) of greater than 30, is a major health concern in the United States and other countries; it has been estimated that one in three Americans and more than 300 million people world-wide are obese. Complications of obesity include many serious and life-threatening diseases, including hypertension, diabetes, coronary artery disease, stroke, congestive heart failure, pulmonary insufficiency, multiple orthopedic problems, various cancers, and a markedly decreased life expectancy. Intentional weight loss, however, can improve many of these medical complications associated with obesity.

While weight loss can improve many of the medical complications associated with obesity, its management as a health concern has proven troublesome. A variety of approaches, including dietary methods, psychotherapy, behavior modification, and pharmacotherapy have each met with some success but as a whole failed to effectively control the rapid growth in the incidence and severity of obesity seen in the United States. The severity of problems associated with obesity also has led to the development of several drastic surgical procedures. One such procedure physically reduces the size of the stomach so that a person cannot consume as much food as was previously possible. These stomach reduction surgeries had some limited early success, but now it is known that the stomach can stretch back to a larger volume over time, limiting the achievement of sustained weight loss in many individuals. Another drastic surgical procedure induces the malabsorption of food by reducing the absorptive surface of the gastrointestinal (GI) tract, generally through by-passing portions of the small intestine. This gastric by-pass procedure has also been combined with stomach reduction surgery. While these described surgical procedures can be effective to induce a reduction in food intake and/or overall weight loss in some, the surgical procedures are highly invasive and cause undue pain and discomfort. Further, the described procedures may result in numerous life-threatening postoperative complications. These surgical procedures are also expensive, difficult to reverse, and place a large burden on the national health care system.

Non-surgical approaches for the treatment of obesity also have been developed. For example, one non-surgical endoscopic approach to treating obesity includes the placement of a gastric balloon within the stomach. The gastric balloon fills a portion of the stomach, providing the patient with a feeling of fullness, thereby reducing food intake. This approach has yet to be convincingly shown to be successful, however, and a number of problems are associated with the gastric balloon device, including poor patient tolerance and complications due to rupture and/or migration of the balloon. Other non-surgical devices designed to induce weight loss limit the absorption of nutrients in the small intestine by funneling food from the stomach into a tube found within the small intestine so that the food is not fully digested or absorbed within the small intestine. While this type of device may be somewhat effective at limiting the absorption of consumed food, there is still room for a variety of improvements in non-surgical devices designed to induce weight loss and/or a reduction in food intake.

An understanding of biological events that contribute to the creation of satiety signals provides an opportunity to develop "smart" nonsurgical devices that can trigger such events. The amount of food that individuals consume is largely dependent on biological signals between the gut and the brain. Specifically, hormonal signals from the gut to the brain are correlated with both the onset and cessation of food intake. While increased levels of hormones, such as ghrelin, motilin and agouti-related peptide, are involved in the promotion of appetite and the onset of food intake, increased levels of a number of other hormones are involved in the cessation of food intake.

Various biologic events contribute to the physiologic cessation of food intake. Generally, as a meal is consumed, the ingested food and by-products of digestion interact with an array of receptors along the GI tract to create satiety signals. Satiety signals communicate to the brain that an adequate amount of food has been consumed and that an organism should stop eating. Specifically, GI tract chemoreceptors respond to products of digestion (such as sugars, fatty acids, amino acids and peptides) while stretch receptors in the stomach and proximal small intestine respond to the physical presence of consumed foods. Chemoreceptors respond to the products of digestion by causing the release of hormones or other molecular signals. These released hormones and/or other molecular signals can stimulate nerve fibers to send satiety signals to the brain. The arrival of these signals in the brain can trigger a variety of neural pathways that can reduce food intake. The released hormones and/or other molecular signals can also travel to the brain themselves to help create signals of satiety. Mechanoreceptors generally send satiety signals to the brain through stimulation of nerve fibers in the periphery that signal the brain.

The present invention provides methods and devices that help to reduce food intake by providing non-surgical devices and methods that trigger the aforementioned biological events that contribute to the creation of satiety signals.

SUMMARY OF THE DISCLOSURE

Described herein are intragastric devices, designed, for example, to help reduce food intake.

In general, in one embodiment, a method of loading an unsheathed endolumenal device into a working channel of an endoscope includes: (1) attaching an adaptor to a handle of the endoscope such that a channel of the adaptor is in communication with the working channel of the endoscope; (2) loading the unsheathed endolumenal device into a lumen of a loading tool from a coupling end of the loading tool an open end of the loading tool until a proximal end of the device is positioned at the open end; (3) connecting the coupling end of the loading tool to the adaptor; and (4) pushing the proximal end of the unsheathed endolumenal device distally along the lumen of the loading tool through the adaptor and into the working channel.

This and other embodiments can include one or more of the following features. Loading the unsheathed device can include loading such that a distal end of the device remains outside of the loading tool. The method can further include advancing the distal end of the unsheathed endolumenal device into the channel of the adaptor. The method can further include removing the loading tool from the adaptor and continuing to push the proximal end of the unsheathed endolumenal device distally until the unsheathed endolumenal device is completely within the working channel. Pushing the proximal end of the unsheathed endolumenal device can include pushing until the proximal end of the device is between 0 mm and 5 mm within the channel of the adaptor, and the removing step can include removing after the pushing step. The method can further include placing an introducer through the channel of the adaptor such that a portion of the introducer extends into the working channel, and pushing the proximal end of the unsheathed endolumenal device distally through the channel of the adaptor can include pushing the device through a lumen of the introducer. The portion of the introducer that can extend into the working channel can be an angled tip. Loading can include using graspers to pull on a proximal end of the endolumenal device. Attaching the adaptor can include snapping the adaptor around the handle. Attaching the adaptor to the handle can include attaching the adaptor and handle such that the adaptor can be fixed in position relative to the endoscope.

In general, in one embodiment, a method of delivering an unsheathed endolumenal device into a body lumen includes: (1) advancing an unsheathed endolumenal device into a working channel of an endoscope; (2) advancing the endoscope through the body lumen until a distal end of the working channel is positioned at a first delivery position within the body lumen; (3) while maintaining the distal end of the working channel at the first delivery position, advancing the unsheathed endolumenal device distally out of the working channel and along the body lumen until a first delivery marker on the endolumenal device is observed; (4) after the first delivery marker is observed, advancing the unsheathed endolumenal device out of the working channel while withdrawing the endoscope from the bodily lumen; and (5) continuing to advance until the unsheathed endolumenal device is completely released from the working channel of the endoscope.

This and other embodiments can include one or more of the following features. The method can further include stopping the advancing and withdrawing step when a second delivery marker is observed and confirming a portion of the endolumenal device is in a desired position relative to the body lumen based upon placement of the second delivery marker at a second delivery position within the body lumen. The second delivery position can be a duodenal bulb adjacent to a pylorus. The method can further include withdrawing the endolumenal device and endoscope proximally if the second marker is distal of the second delivery position. The second delivery marker can be a bulking feature over a wire portion of the device. The first delivery marker can be a portion of the device that is a different color than a second portion of the device. The endoscope can be a gastroscope. The first delivery position can be a third portion of the duodenum. Continuing to advance can include advancing the unsheathed endolumenal device such that a distal end of the device is in a fourth portion of the duodenum.

In general, in one embodiment, a system for delivering an endolumenal device through an endoscope includes a delivery tool and an adaptor. The delivery tool has an elongate tube configured to hold a portion of the endolumenal device therein and a first connecting feature on a distal end of the elongate tube. The adaptor is configured to attach to a handle of the endoscope. The adaptor includes a channel therethrough and a second connecting feature configured to mate with the first connecting feature of the delivery tool. The elongate tube of the delivery tool is configured to align with the channel of the adaptor when the first and second connecting features are mated.

This and other embodiments can include one or more of the following features. The system can further include an introducer having a tubular member that can be configured to extend through the channel of the adaptor and into the working channel of the endoscope. The tubular member can have an angled end configured to extend into the working channel. The introducer can further include a pin configured to mate with a slot in the adaptor. The pin and slot can further be configured to orient the angled end within the working channel. The adaptor can include a first component and a second component. The first and second components can be configured to snap together around a portion of the endoscope handle. The connecting feature can include a first pin and a second pin, and the adaptor can include a first bore in the first component and a second bore in the second component. The first pin can be configured to fit within the first bore, and the second pin can be configured to fit within the second bore when the first and second connecting features are mated. The first and second connecting features can be snapping features.

In general, in one embodiment, an intragastric device includes a wire elongated member, a wire anchor, and a bulking component covering a portion of the elongated member or the anchor. The bulking component includes spiral cut tubing.

This and other embodiments can include one or more of the following features. The intragastric device can further include a sleeve attached to the elongated member at a distal end thereof. The sleeve can be configured to slide distally along the elongated member to form a plurality of radially expanded flow reduction elements. The bulking component can cover a portion of the elongated member and can be positioned such that, when the sleeve is unexpanded, a gap of 0.5 inches or less is between the bulking component and a proximal end of the sleeve. The bulking component can include polyethylene terephthalate tubing. The spiral can have a pitch of between 0.05 inches and 0.25 inches. The pitch can be approximately 0.125 inches. An inner diameter of the bulking component can be greater than an outer diameter of the portion of the elongated member or the anchor such that there is a gap therebetween. The bulking component can be attached to the wire only at an end of the spiral cut tubing. The bulking component can be attached to the portion of the elongated member or the anchor with glue. The portion of the elongated member or the anchor can include a groove therein configured to hold glue. The wire elongated member or the wire anchor can include nitinol. The nitinol can be electropolished. The wire can have an outer diameter of between 0.015 inches and 0.030 inches, and the bulking can have an outer diameter of between 0.050 inches and 0.15 inches.

In general, in one embodiment, an intragastric device includes an elongated member, a sleeve attached to the elongated member, and an anchor attached to a proximal end of the elongated member. The sleeve is configured to slide distally along the elongated member to form a plurality of radially expanded flow reduction elements. The elongated member includes two markers thereon. Each of the markers is configured to align with a different portion of the gastrointestinal tract.

This and other embodiments can include one or more of the following features. One of the different portions can be a third portion of the duodenum. One of the different portions can be a duodenal bulb adjacent to the pylorus. At least one of the markers can be a bulking feature over a wire portion of the device. A proximal end of the at least one marker can be positioned such that a distance from the proximal end of the marker to a distal end of the device is approximately equal to a distance from a pylorus to a fourth portion of the duodenum. At least one of the markers can be a portion of the device that is a different color or texture than a second portion of the device. A proximal end of the at least one marker can be positioned such that a distance from the proximal end of the marker to a distal end of the device is approximately equal to a distance from a proximal end of a third portion of the duodenum to a fourth portion of the duodenum. At least one of the markers can be under the sleeve. The elongated member can have a pre-set shape prior to insertion in the gastrointestinal tract, and the elongated member can be configured to return to the pre-set shape after insertion into the gastrointestinal tract.

BRIEF DESCRIPTION OF THE DRAWINGS

FIG. 3A shows the expanded sheath of the insert of FIG. 2A.

FIG. 3B shows a close-up of the proximal end of the sheath of FIG. 3A.

FIGS. 8A-8B show a spiral bulking component on a spine of a gastrointestinal insert. FIG. 8A is a view of the outside while FIG. 8B is a cross-section.

FIG. 10A shows a gastrointestinal insert having a thin coating around a portion thereof. FIG. 10B shows a close-up of the wire and coating of FIG. 10A. FIG. 10C shows a gastrointestinal insert having a swollen wire.

FIGS. 13A-13D show various views of a loading tool of an endolumenal delivery system.

FIGS. 14A-14F show various views of a first side of an adaptor of an endolumenal delivery system.

FIGS. 19-20C show an overtube configured to remove an endolumenal device.

FIGS. 31A-31E shows another embodiment of an anchor.

FIGS. 38A-38E show another embodiment of an anchor.

FIG. 46 shows a cross-section of the proximal end of an endoscope.

FIG. 46A shows a close-up of the introducer of a delivery system within the lumen of the endoscope working channel flange.

FIGS. 48A and 48B show bulking components for the insert of FIG. 2B.

FIGS. 51-51D show exemplary grooves in the wire of the insert of FIG. 2B.

DETAILED DESCRIPTION

Figure 1:
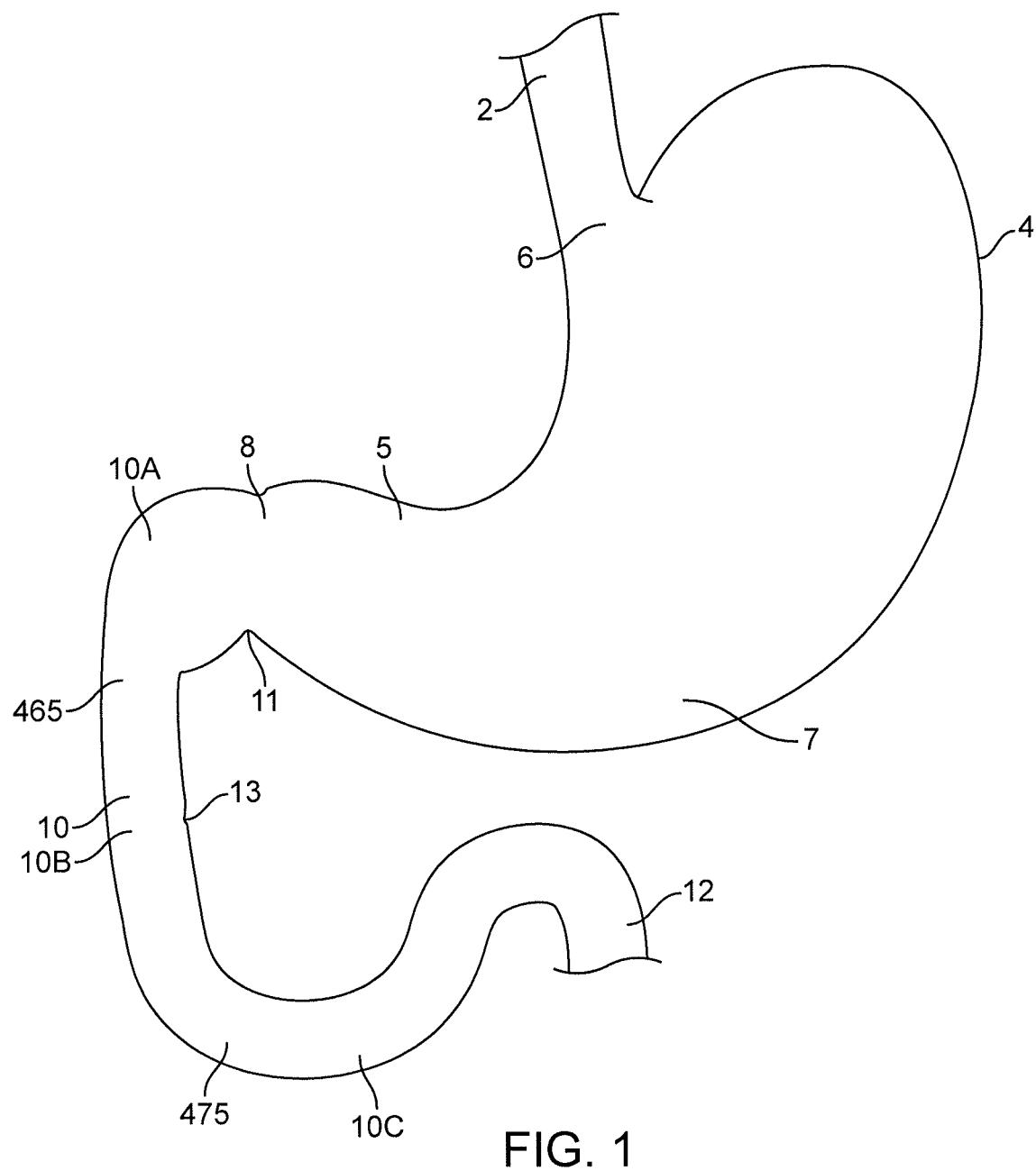
FIG. 1 illustrates the human gastrointestinal tract.

FIG. 1 provides a view of the human gastrointestinal tract, including the stomach 4 and duodenum of the small intestine 10. Important features are the esophagus 2, stomach 4, antrum 7, pylorus 8, pyloric valve 11, duodenum 10, jejunum 12 and ampulla of Vater (or hepatopancreatic ampulla) 13, which is formed by the union of the pancreatic duct and the common bile duct. Functionally, the esophagus 2 begins at the nose or mouth at its superior end and ends at the stomach 4 at its inferior end. The stomach 4 encloses a chamber which is characterized, in part, by the esophageal-gastric juncture 6 (an opening for the esophagus 2) and the antrum-pyloric juncture 5 (a passageway between the antrum 7 through the pylorus 8 to the duodenum 10 of the small intestine). The pylorus 8 controls the discharge of contents of the stomach 4 through a sphincter muscle, the pyloric valve 11, which allows the pylorus 8 to open wide enough to pass sufficiently-digested stomach contents (i.e., objects of about one cubic centimeter or less). These gastric contents, after passing into the duodenum 10, continue into the jejunum 12 and on into the ileum (not shown). The duodenum 10, jejunum 12, and ileum make up what is known as the small intestine. However these individual portions of the alimentary canal are sometimes individually referred to as the small intestine. In the context of this invention the small intestine can refer to all or part of the duodenum, jejunum and/or ileum. The ampulla of Vater 13, which provides bile and pancreatic fluids that aid in digestion, is shown as a small protrusion on the medial wall of the duodenum 10.

Embodiments of the inventive device include various forms that provide stability in a residence site in the gastrointestinal tract, particularly the duodenum. Some embodiments of the device, which may be synonymously referred to as an intestinal insert, are stabilized in the intestine by way of an anchoring member that resides in the stomach and is too large to be swept through the pylorus. In other embodiments, stabilizing features in the intestine may include expanded portions of the device in the duodenal bulb, which is larger than the more distal portion of the duodenum, and which thereby effectively prevents distal movement.

Some embodiments of the device and associated methods of using the device are directed toward reducing the rate of food transit through the intestine by physical mechanisms of intervening in the rate of food transit. In other aspects, embodiments of the invention act by eliciting satiety signals by way of physiological mechanisms, or alternatively, by directly providing satiety signals through bioactive materials or agents or by neuronal stimulation, thereby reducing food intake behaviorally. Some embodiments of the device are directed toward medical purposes broader than satiety and digestive physiology alone, although the satiety and food consumption functionalities of embodiments of the device and method will be described herein in greater detail. As an example of non-obesity or satiety-inducing medical use, some embodiments of the device may be used as an eluting source for bioactive agents, and as such any medically appropriate drug could be delivered by such a device. In some aspects, embodiments of the device may contribute to slowing food transit and/or reducing food intake by the satiety signals generated by the intestine in direct response to the mere physical presence of the device. Such signals could, for example, be mediated by stretch-responsive neurons or mechanoreceptors in the intestinal wall. In other embodiments, satiety signals could be mediated by hormones that are responsive to physical presence of material in the intestine, or which are secondarily responsive to mechanoreceptors. In other embodiments, the slowing of food or the increased residency time, and the consequent change in the chemical environment of the intestine, may elicit responses from chemoreceptors residing in the intestine to signal either neurally or hormonally in such a way that has a net effect of signaling satiety.

In still other embodiments of the invention, the device may convey bioactive material or agents that are released over time within the intestine, the bioactive agents conveying a net signal of satiety. In some embodiments, the bioactive agents with a net satiety signaling effect are passively released from sites such as coatings, depots, or reservoirs within the device. Bioactive materials or agents may include any of hormones, drugs, or cells. In some embodiments, bioactive agents may be held in osmotic pumps and released by osmotic drive. Release mechanisms, such as osmotic pumps, provide a level of control and predictability to bioactive agent release, but the mechanism remains relatively passive and without means of intervention. Other embodiments of the invention, however, may include more active mechanisms for bioactive agents release or delivery, as could be provided by electrically driven pumps or by piezoelectric elements that allow or promote the release stored bioactive agents in response to applied current. Such devices may include power storage elements, or may be provided power by external sources by wired or wireless approaches.

In still other embodiments of the invention, the device may include electrodes or conductive elements that provide electrical stimulation to nerves in the intestine, such resulting neural activity contributing to a net effect of signaling satiety to the brain. In some embodiments, satiety-related neuronal activity may further be mediated by endocrine mechanisms. As in embodiments of the invention with powered mechanisms for bioactive agent release, embodiments with electrical capability may include power storage devices or be enabled to receive energy conveyed from external sources.

In other aspects of the invention, embodiments of the inserted device, with or without an anchor, may provide a platform for bioactive agent delivery, neural stimulus delivery, or radiation therapy delivery for medical purposes more broad than inducing satiety or intervening in food transit. For the delivery of some bioactive agents, there may be considerable advantage associated with local delivery of an agent to an intestinal site. Such advantages may include localization of dosing, lack of exposure to stomach acid as occurs in oral delivery or diminished exposure to the metabolic machinery of the liver and kidney that i.v. drug delivery, or any form of systemic delivery faces. Further, embodiments of the device may accommodate multiple drugs; in some embodiments the release of such multiple drugs may be independently controlled.

The description now addresses the digestive system, the digestive process, and aspects of the endocrinology and neurophysiology of satiety as they relate to embodiments of the invention. The adult duodenum is about 20-25 cm long and is the shortest, widest, and most predictably placed part of the small intestine. The duodenum forms an elongated C-shaped configuration that lies between the level of the first and third lumbar vertebrae in the supine position. Susan Standring (ed.), Gray's Anatomy, 39$^{th}$ Ed., 1163-64 (2005), provides a standard reference. Returning to FIG. 1 for reference and further detail of aspects of the digestive system, the first portion of the duodenum, often referred to as the duodenal bulb 10a, is about 5 cm long and starts as a continuation of the duodenal end of the pylorus 8. This first portion of the duodenum passes superiorly, posteriorly and laterally for 5 cm before curving sharply inferiorly into the superior duodenal flexure 465, which marks the end of the first portion of the duodenum. The second portion of the duodenum, often called the vertical duodenum 10b, is about 8-10 cm long. It starts at the superior duodenal flexure 465 and runs inferiorly in a gentle curve towards the third lumbar vertebral body. Here, it turns sharply medially into the inferior duodenal flexure 475, which marks its junction with the third portion of the duodenum. The third portion of the duodenum, often called the horizontal duodenum 10c, starts at the inferior duodenal flexure and is about 10 cm long. It runs from the right side of the lower border of the third lumbar vertebra, angled slightly superiorly, across to the left and ends in continuity with the fourth portion of the duodenum in front of the abdominal aorta. The fourth portion of the duodenum is about 2.5 cm in length. It starts just to the left of the aorta and runs superiorly and laterally to the level of the upper border of the second lumbar vertebra. It then turns antero-inferiorly at the duodenojejunal flexure and is continuous with the jejunum.

The digestive process starts when consumed foods are mixed with saliva and enzymes in the mouth. Once food is swallowed, digestion continues in the esophagus and in the stomach, where the food is combined with acids and additional enzymes to liquefy it. The food resides in the stomach for a time and then passes into the duodenum of the small intestine to be intermixed with bile and pancreatic juice. Mixture of the consumed food with bile and pancreatic juice makes the nutrients contained therein available for absorption by the villi and microvilli of the small intestine and by other absorptive organs of the body.

Robert C. Ritter, author of "Gastrointestinal mechanisms of satiation for food", published by Physiology & Behavior 81 (2004) 249-273, summarizes our understanding of the various means the gastrointestinal tract uses to control appetite. He states that the role of the stomach in satiation is to sense the volume of ingesta arriving from a meal and to produce a variety of signaling substances that may be involved in satiation. It is, however, the small intestine specifically that receives these signals. Further, it is the intestine that responds to the energy density of ingesta, limiting further gastric emptying and signally satiety when adequate calories have passed. Through analysis of the location of afferent nerves (p. 255), Ritter shows that vagal nerve afferents are most concentrated in the duodenum and least concentrated more distally in the ileum. This early concentration of afferents will moderate appetite early in the eating process. The timeliness of the response to nutrient intake has been further demonstrated by others in a variety of mammals including monkeys, rats and humans. It is clear that the reduction in food intake begins within minutes of the start of intake and that this reduction is not therefore a response to postabsorptive or systematic metabolic effects. These passages of Ritter are specifically incorporated herein by reference as relates to the positioning of the devices described herein or for the placement and size of flow reduction elements of embodiments of the present invention.

The presence of partially digested food within the stomach and small intestine initiates a cascade of biological signals that create satiety signals principally emanating from the proximal small intestine that contribute to the cessation of food intake. One such satiety signal is initiated by the release of cholecystokinin (CCK). Cells of the small intestine release CCK in response to the presence of digested foods, and in particular, in response to dietary fat, fatty acids, small peptides, and amino acids. Elevated levels of CCK reduce meal size and duration and may do so through a number of different mechanisms. For example, CCK may act on CCK-A receptors in the liver and within the central nervous system to induce satiety signals. CCK stimulates vagal afferent fibers in both the liver and the pylorus that project to the nucleus tractus solitarius, an area of the brain that communicates with the hypothalamus to centrally regulate food intake and feeding behavior. CCK also stimulates the release of enzymes from the pancreas and gall bladder and inhibits gastric emptying. Because CCK is a potent inhibitor of gastric emptying, some of its effects on limiting food intake may be mediated by the retention of food in the stomach.

Cells of the small intestine (particularly L cells) also release glucagon-like peptide 1 (GLP-1) and oxyntomodulin (OXM) in response to nutrient signals of digestion. Elevated levels of GLP-1 and OXM are associated with satiety signals and the cessation of food intake. These hormones may signal satiety by activating receptors on afferent vagal nerves in the liver and/or the GI tract and/or by inhibiting gastric emptying.

Pancreatic peptide (PP) is released in proportion to the number of calories ingested, and in response to gastric distension. Elevated levels of PP have been shown to reduce food intake and body weight. PP may exert some of its anorectic effects via vagal afferent pathways to the brainstem, as well as through more local effects, such as by suppression of gastric ghrelin production.

Peptide YY$_{3-36}$ (PYY$_{3-36}$) is another biological signal whose peripheral release may be correlated with reduced food intake and/or the cessation of eating. Specifically, low levels of PYY$_{3-36}$ have been correlated with obesity while its administration decreases caloric intake and subjective hunger scores. Intravenous administration of PYY$_{3-36}$ may reduce food intake through its effects of suppressing ghrelin expression, delaying gastric emptying, delaying various secretion from the pancreas and stomach and increasing the absorption of fluids and electrolytes from the ileum after a meal.

Insulin and leptin are two additional biological signals that regulate satiety and eating behavior. Through parasympathetic innervation, beta cells of the endocrine pancreas release insulin in response to circulating nutrients such as glucose and amino acids, and in response to the presence of GLP-1 and gastric inhibitory peptide (GIP). Insulin stimulates leptin production from adipose tissue via increased glucose metabolism. Increased insulin levels in the brain leads to a reduction in food intake. Elevated leptin levels also decrease food intake and induce weight loss. Insulin and leptin have also been implicated in the regulation of energy expenditure since their administration induces greater weight loss than can be explained by reduction in food intake alone. Both insulin and leptin act within the central nervous system to inhibit food intake and to increase energy expenditure, most likely by activating the sympathetic nervous system. Insulin's effects to decrease food intake also involve interactions with several hypothalamic neuropeptides that are also involved in the regulation of feeding behavior such as, by way of example, NPY and melanocortin ligands.

Other hormones or biological signals that are involved in the suppression or inhibition of food intake include, by way of example, GIP (secreted from intestinal endocrine K cells after glucose administration or ingestion of high carbohydrate meals; enterostatin (produced in response to dietary fat; amylin (co-secreted with insulin from pancreatic beta cells); glucagon, gastrin-releasing peptide (GRP), somatostatin, neurotensin, bombesin, calcitonin, calcitonin gene-related peptide, neuromedin U (NMU), and ketones.

In relation to embodiments of the present invention, when the passage of partially digested food or chyme is partially impeded within the duodenum of the small intestine and the flow rate through this area is reduced (or to express the same phenomenon in another way, as residency time is increased), the emptying of the stomach and the duodenum will occur more slowly. This slowing, by itself, may create extended feelings of satiety and thus lead to a decrease in food intake (due to the longer retention time of food in the stomach). The slowing of the passage of food also provides more time for the partially digested food to interact with chemoreceptors, stretch receptors, and mechanoreceptors along the GI tract so that stimulation of satiety signals may be increased and/or prolonged, which may, in turn, lead to a reduction in food intake during an eating period and/or longer periods between food intake.

In addition to keeping partially-digested food within the small intestine for an extended period of time, the methods and devices of the present invention may also enhance and/or prolong the release of satiety signals by releasing signals into the small intestine themselves. For example, in some embodiments, the methods and devices of the present invention may release nutrient products of digestion to stimulate chemoreceptors to cause the release of hormones and/or other molecular signals that contribute to the creation of satiety signals. In another embodiment, the methods and devices of the present invention may exert a small amount of pressure on the walls of the GI tract to stimulate stretch (mechanoreceptors) to generate and send satiety signals to the brain. In another embodiment, the methods and devices of the present invention may release signals, such as, by way of example, nutrient by-products of digestion of food, to stimulate chemoreceptors as described above and may exert a small amount of pressure on the walls of the small intestine, as described above, to contribute to the generation of satiety signals.

Figure 2A:
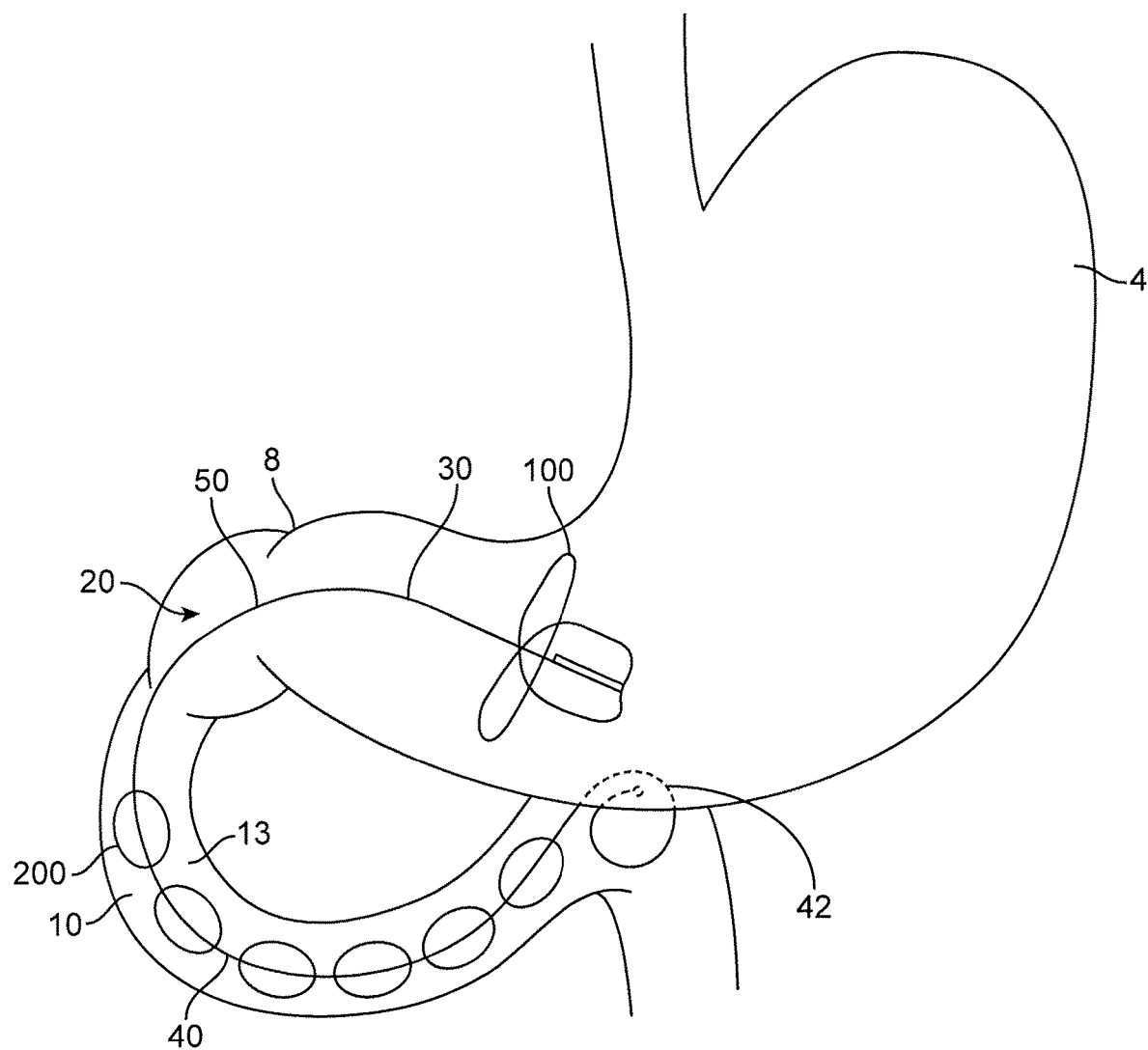
FIG. 2A shows an embodiment of a gastrointestinal insert implanted within the gastrointestinal tract.
Figure 2B:
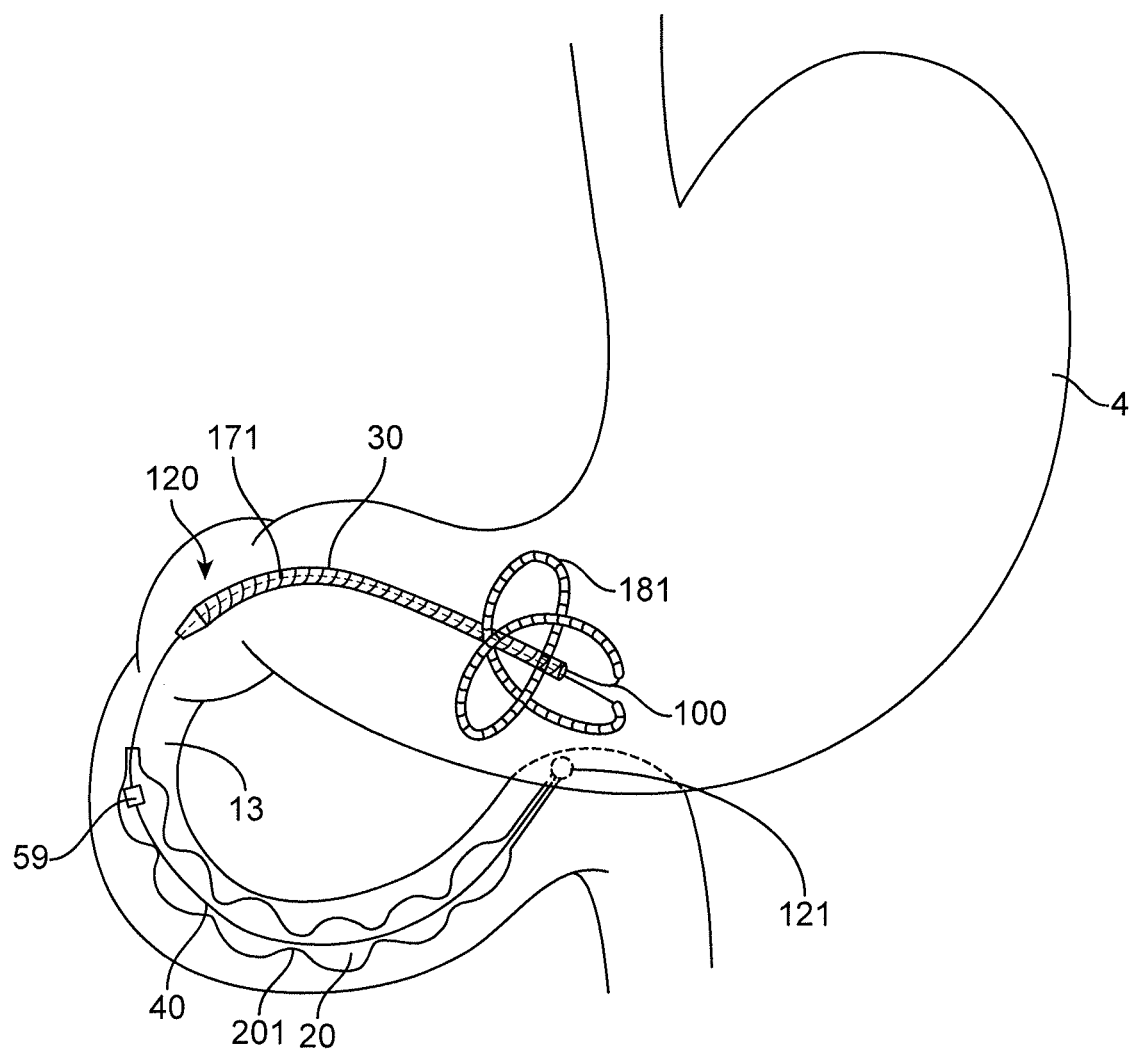
FIG. 2B shows another embodiment of a gastrointestinal insert implanted within the gastrointestinal tract.

Turning now to embodiments of the invention, FIGS. 2A and 2B show small intestinal inserts 20, 120 made in accordance with the present invention that may contribute to the creation of satiety signals. Referring to FIG. 2A, the insert 20 is positioned in the stomach 4 and small intestine 10. The insert 20 has a proximal portion 30 and a distal portion 40, and a central spine 50 that extends from the proximal portion 30 to the distal portion 40. One or more flow reduction elements 200 that are sized to fit within the small intestine 10 may be attached to the central spine 50. The central spine 50 has an anchoring member 100 near its proximal end, with the anchoring member 100 securing the proximal end of the central spine 50 in the stomach. The anchoring member 100 is sized so that it will not pass through the pylorus 8. In this way, embodiments of the present invention including an anchoring member anchor the flow reduction elements 200 within the small intestine. A pigtail 42 provides an atraumatic distal end to the spine 40.

Referring to FIG. 2B, the insert 120 is similar to insert 20 except that a bulking component 171 is shown over the spine 50, a bulking component 181 is shown over the anchor 100, the flow reduction elements 200 are shown as part of an expandable sleeve 201, and the distal end of the spine 50 includes a straight atraumatic feature 121 rather than a pigtail 42.

Figure 3:
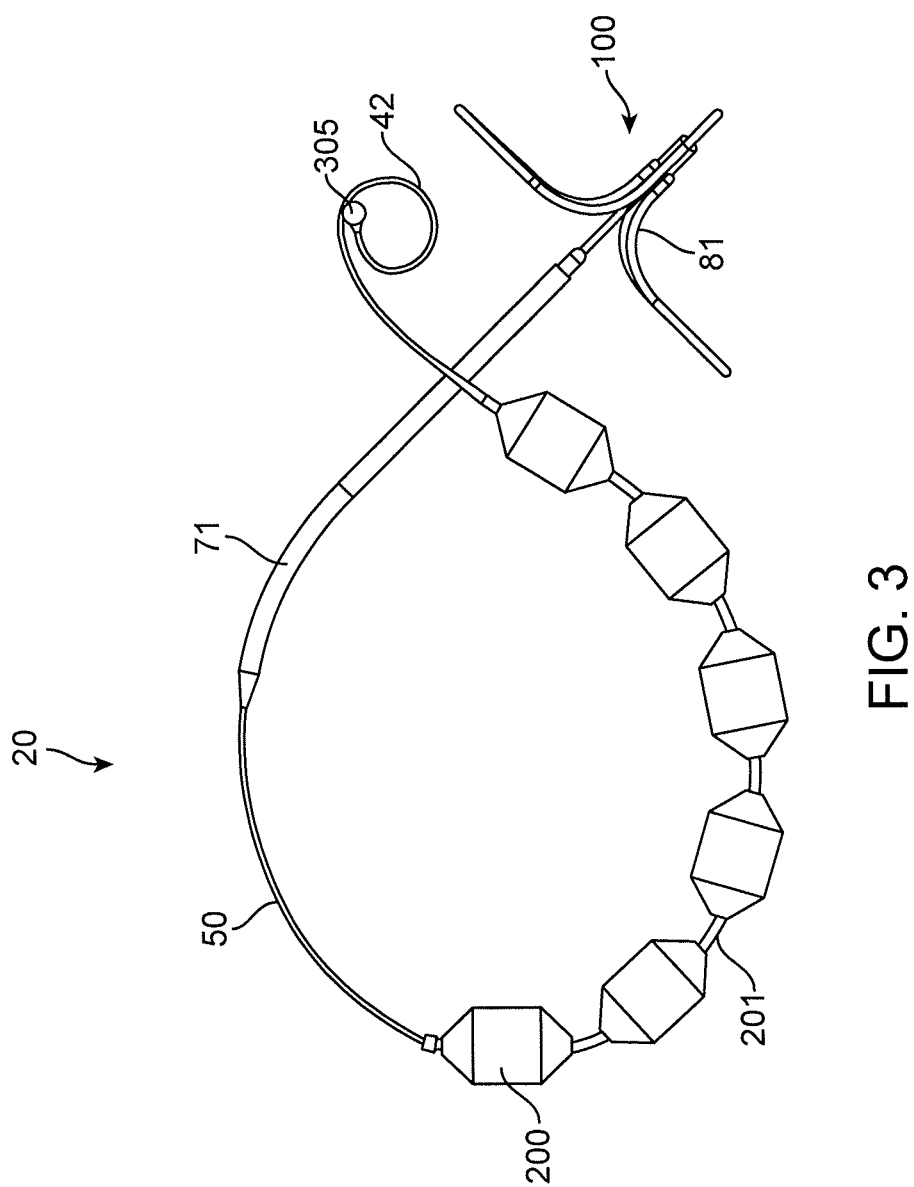
FIG. 3 is a detailed view of the insert of FIG. 2A.
Figure 4A:
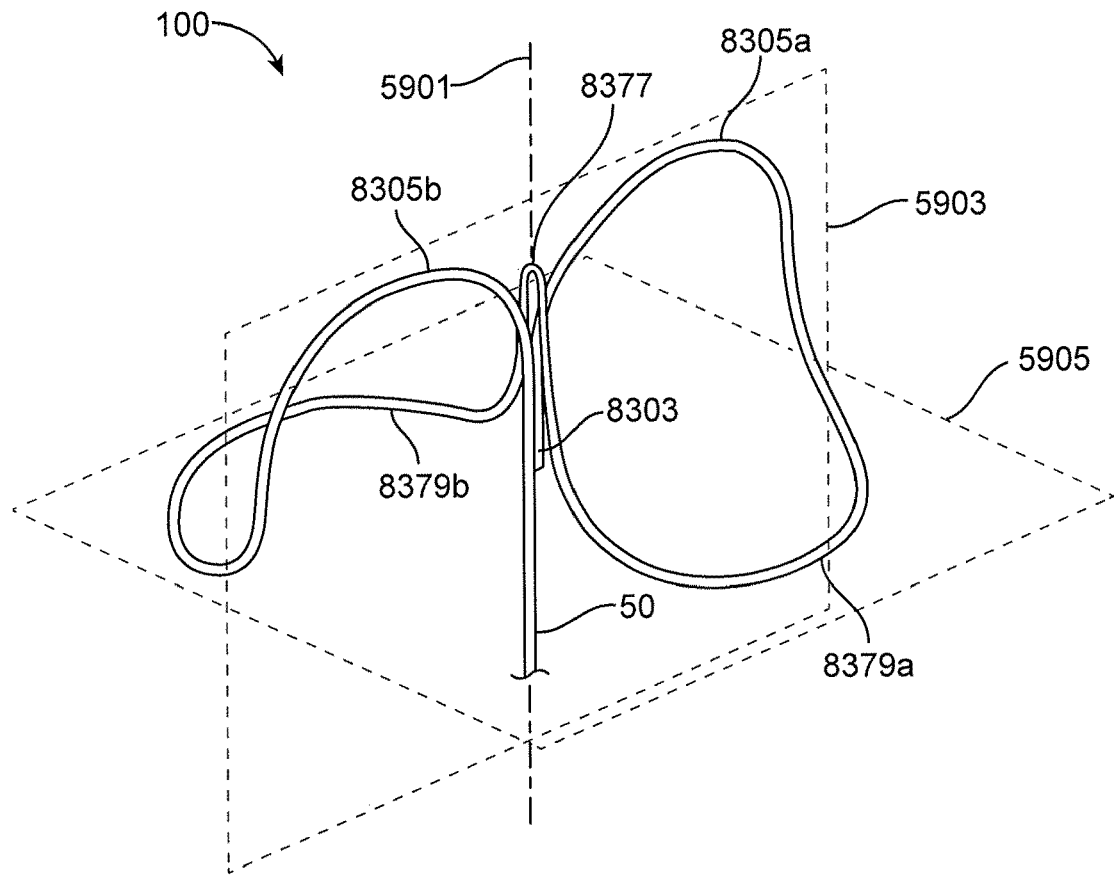
FIGS. 4A-4E show close-ups of the proximal anchor of the insert of FIG. 2A.
Figure 4B:
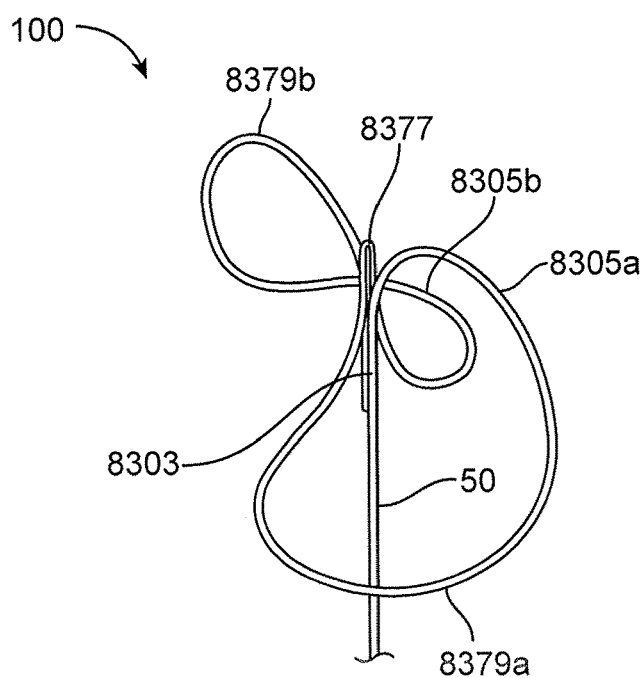
Figure 4C:
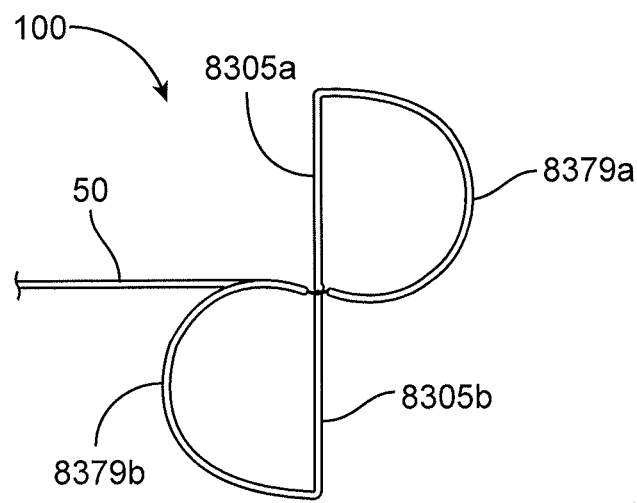
Figure 4D:
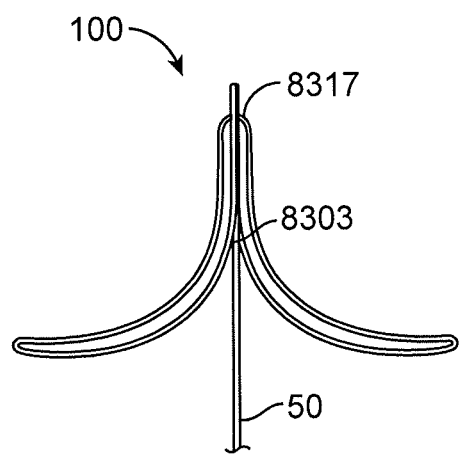
Figure 4E:
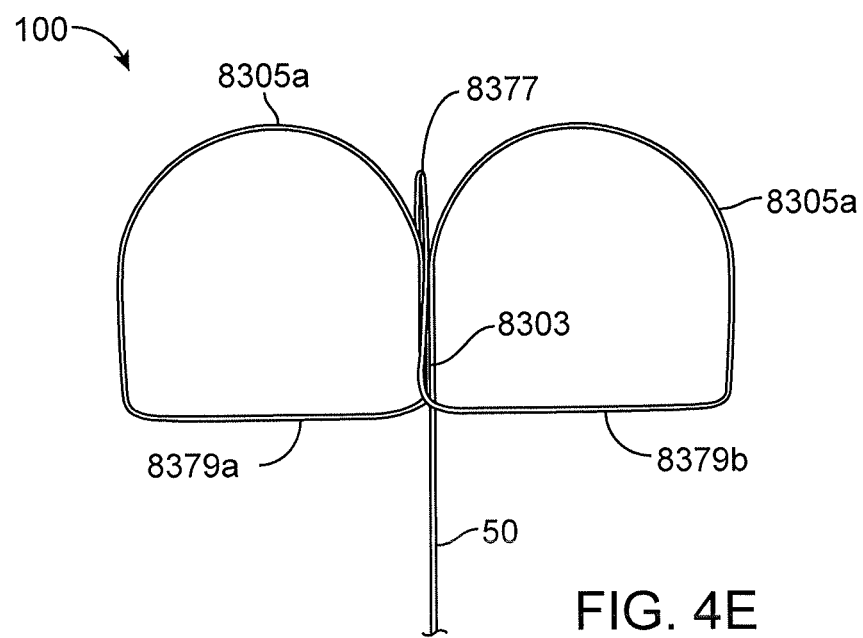

FIG. 3 shows a more detailed view of the insert 20. The insert 20 includes flow reduction elements 200 that are formed along an elongate spine 50. An anchor 100 is attached to the proximal end. The insert 20 includes one or more features designed to minimize tissue interaction of the insert 20 when implanted in the gastrointestinal tract, such as a spine bulking component 71 and/or an anchor bulking component 81, as discussed further below. A pigtail 42 and distal ball 305 on the distal end of the spine 50 can also prevent the end of the spine 50 from damaging tissue as the insert 20 is delivered and during residency in the GI tract.

Referring to FIGS. 3A-3B, the flow reduction elements 200 can be part of a sleeve 201 configured to radially expand at predetermined locations. The sleeve 201 can be formed, for example, of braided polyethylene terephthalate filament. The sleeve 201 can be fused to the spine 50 at a distal attachment point 203. A tubular sliding element 205 can be attached to the sleeve 201 at the proximal end thereof to allow the sleeve 201 to slide along the spine 50 to expand the flow reduction elements 200. The spine can further include a stopper 59 (see FIG. 7 or 2B) configured to prevent the sleeve 201 from moving too far distally.

Embodiments of flow reduction elements 200 may assume many configurations, and may vary further with regard to physical features such as composition, nature of the surface, and porosity of the bulk material. Exemplary flow reduction elements are described in U.S. patent application Ser. No. 13/666,919, filed Nov. 1, 2012, titled "DUODENAL GASTROINTESTINAL DEVICES AND RELATED TREATMENT METHODS," now U.S. Patent Application Publication No. 2013-0109912-A1, incorporated by reference herein. A functional property that embodiments of flow reduction elements have in common is that they slow the transit of digesting food without blocking it, and within clinically appropriate guidelines. The process of slowing the transit rate may also have effects on the composition of the digesting food material, such as varying its biochemical profile with regard to the nutritional compounds being metabolized. Chemical receptors and nerves of the duodenum are sensitive to the biochemical profile of metabolites within the chyme, and participate in the coordination of physiology of digestion and satiety and hunger, accordingly. As such, by altering the flow rate, and hence the biochemical profile of chyme, embodiments of the inventive small intestinal insert contribute to the generation of signals associated with satiety. Flow reduction elements may further effect the composition of the digesting food material by the mixing action the flow reduction elements may provide.

FIGS. 4A-4E show a close-up of the proximal anchor 100. The anchoring member 100 can include a stem 8303 extending axially away from the spine 50. The stem 8303 can include two wire portions running substantially parallel to one another. Two arches 8305a,b extend radially away from the stem 8303, two counterarches 8379a,b extend from the arches 8305a,b and a pull loop 8377 connects the counterarches 8379a,b.

The proximal anchor 100 can take approximately the shape of a Figure-8, especially when viewed in an axial manner from a proximal viewpoint. Each arch 8305a,b extends proximally from the stem 8303, curves through a proximal peak, and extends distally to merge into a respective counterarch 8379a,b. The arches 8305a,b can extend both longitudinally and radially away from the stem 8303. This arching form can advantageously provide hoop strength by helping to center the anchor 8301 when the anchor 100 is pushed or compressed from the side. The Figure-8 shape of the anchor 100 can advantageously prevent tangling during delivery and removal because the free length of the wire is minimized and there are no overlapping portions to get tangled.

The counterarches of anchor 100 are shown as peaking or lying in a plane that is substantially perpendicular (90 degree angle) to the axis of the stem. In some embodiments, the counterarches of the anchor 100 can be angled at more than a 90 degree angle relative to the top of the stem, such as 120 degrees (i.e. could extend below the plane perpendicular to the stem shown in FIG. 4A). Such an increased angle could advantageously help prevent the counterarches from flipping up and over the arches during delivery and use.

The arches 8305a,b can both extend counterclockwise (from the proximal point of view) as they merge into the counterarches 8379a,b. Further, the arches 8305a,b are configured to extend in substantially opposite radial directions. Having the arches 8305a,b extend in substantially opposite radial directions advantageously enables the arches 8305a,b to behave as moment arms and assume approximately half of the imparted load in a balanced manner. The opposing direction also helps stabilize forces imparted on the anchor, as each arch will counteract movement of the other in an opposing direction.

The pull loop 8377 can extend in between the arches 8305a,b as they meet at the stem 8303. Further, the pull loop 8377 can merge on both sides into counterarch portions 8379a,b, which then curve upwards into the arches 8305a,b. The peak of the counterarch portions 8379a,b can extend distally and in substantially opposite radial directions from one another. Further, the counterarch portions 8379a,b can be located approximately 90 degrees away from each arch 8305a,b. This placement at 90 degrees provides for approximately four supports—at every 90 degrees around the circumference of the anchor 8301—to stabilize the anchor 8301 and discourage proximal movement of the anchor 8301. The counterarch portions 8379a,b can both loop in the same clockwise/counterclockwise direction from the pull-wire 8377 (viewing the anchor from the proximal end) to connect to the arches 8005a,b).

In some embodiments, the stem 8303, arches 8305a,b, counterarches 8379a,b, spine and pull loop 7077 can be formed of a continuous piece of wire that is joined at the stem. The stem 8303, arches 8305a,b, counterarches 8379a,b, spine and/or pull loop 7077 can be joined together using, for example, welding, crimping, gluing, soldering, sleeving or a combination of these.

To remove the anchor, the pull loop 8377 can act as a "handle" that can be pulled axially in a proximal direction with a retraction tool, such as a grasper, into an endoscope or removal tube. As the pull loop 8377 is pulled in a direction opposite the proximal anchor, anchoring member 8301 collapses radially inwards: counterarches 8379a,b lift up and around the arches 8305a,b, until the arches straighten and collapse as well. The anchor 100 can advantageously be collapsed for delivery or retraction through the esophagus, into the endoscope working channel, and/or into an overtube.

Figure 11:
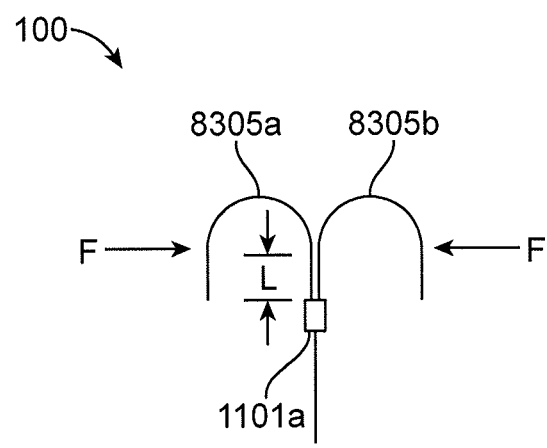
FIGS. 11 and 12 show exemplary connection points of the distal end of the stem of a gastrointestinal insert to the proximal end of the spine of the insert.
Figure 12:
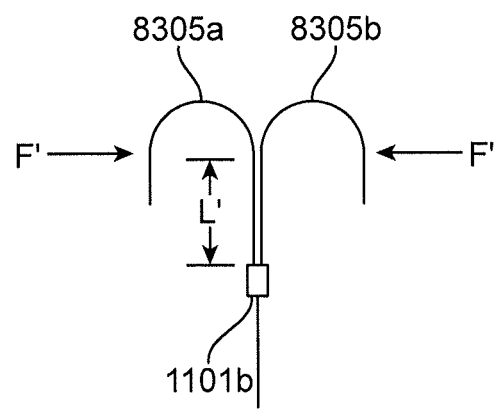
Figure 15C:
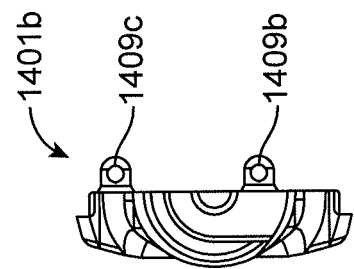
FIGS. 15A-15E show various views of a second side of an adaptor of an endolumenal delivery system.
Figure 15E:
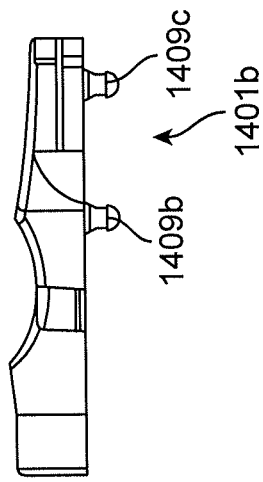
Figure 15B:
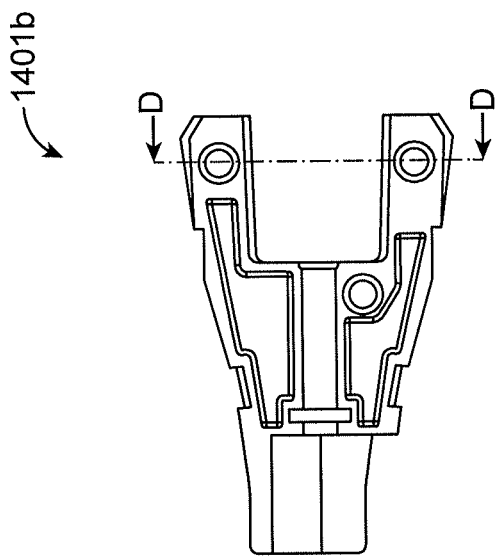
Figure 15D:
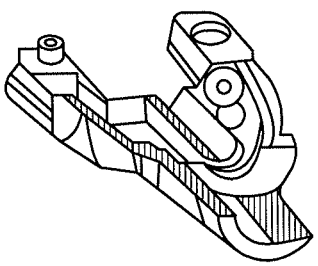
Figure 15A:
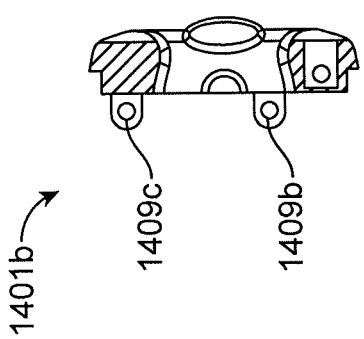
Figure 16B:
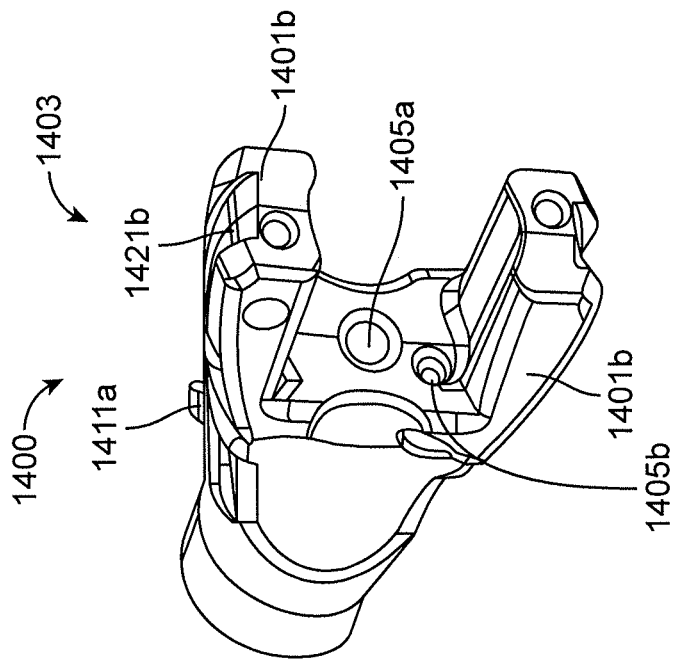
FIGS. 16A-16B show various views of the first and second sides shown in FIGS. 14A-14F and 15A-15E connected together.
Figure 16A:
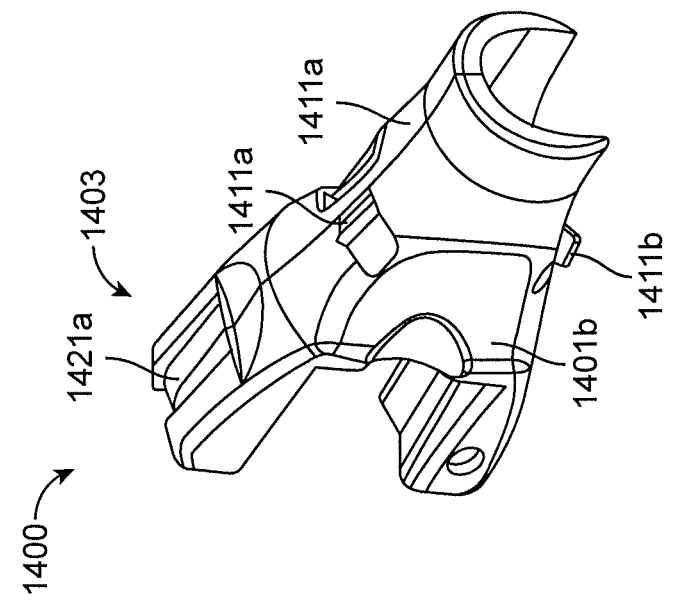

Referring to FIG. 11, in some embodiments, the arches 8305a and 8305b can be joined together at a connection point 1101a that is proximate to the distal ends of the arches 8305a,b. Referring to FIG. 12, in other embodiments, the arches 8305a,b can be joined together at a connection point 1101b that is separated from the ends of the arches 8305a,b by a distance L of between 0.5" and 1.0". The increased distance shown in FIG. 12 can advantageously create more of a moment arm between the arches 8305a,b, thereby increasing the flexibility of the anchor 100 (such as "squeezability" of the anchors in a radial direction) without substantially reducing the pull-out force. Allowing the arches 8305a,b to scissor or overlap with respect to each other, while preventing any individual arch 8305a,b from reducing in diameter, helps to minimize tissue interaction during stomach contractions while maximizing pull-out strength. Further, the connection point 1101 can be crimped, welded, or otherwise connected together.

The wire used to form the spine 50 of the device 20 can have a diameter of less than 0.04", such as less than 0.03", less than 0.02", or approximately 0.018". Using a diameter of less than 0.04" advantageously ensures that the spine 50 is not too stiff, thereby allowing the anchor 100 to move relative to the spine 50 and help avoid constant pressure on gastric tissue during use.

Figure 7A:
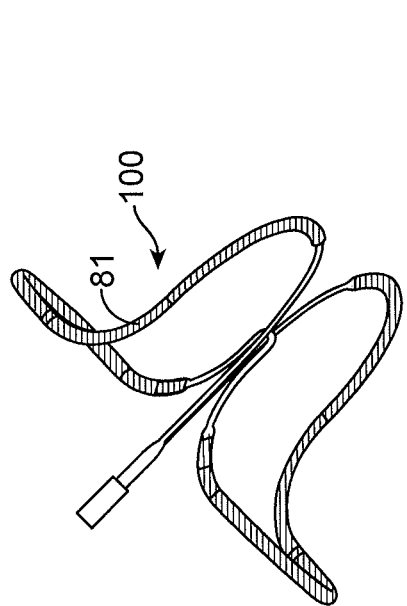
FIGS. 7A and 7B show close-up of the anchor with the bulking component.
Figure 7B:
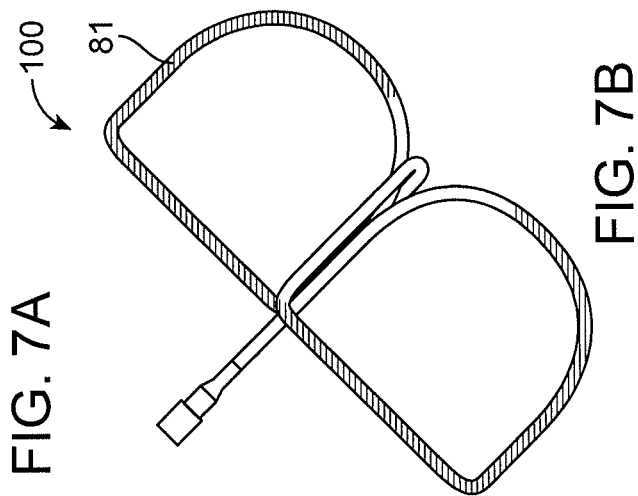
Figure 7:
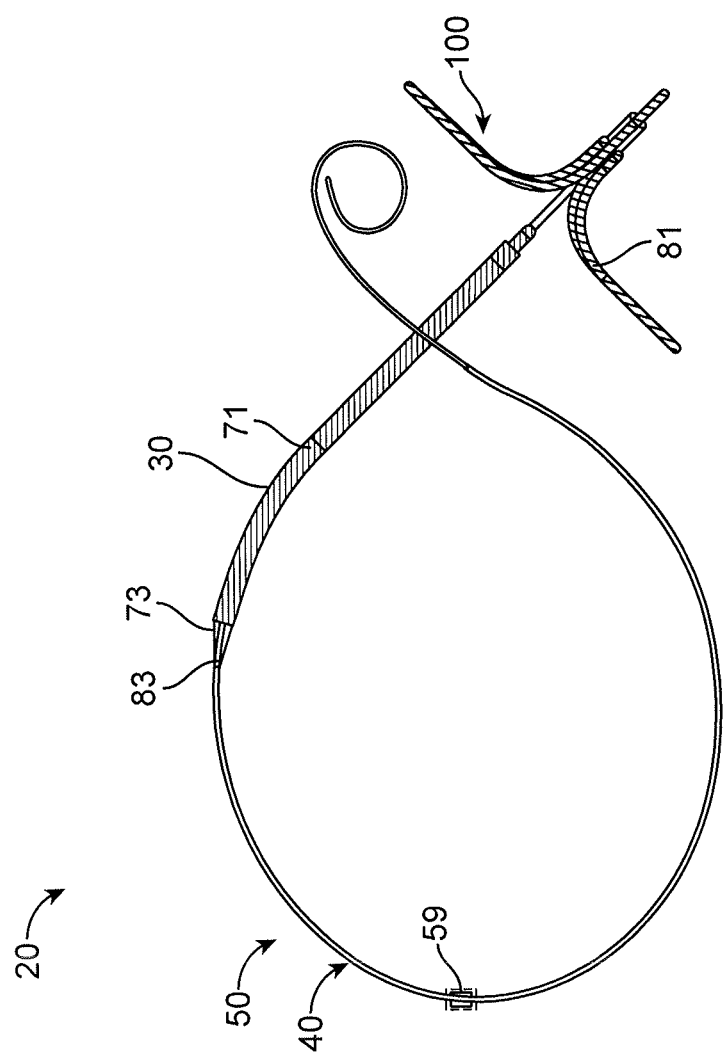
FIG. 7 shows the insert of FIG. 2A with bulking components thereon.
Figure 55:
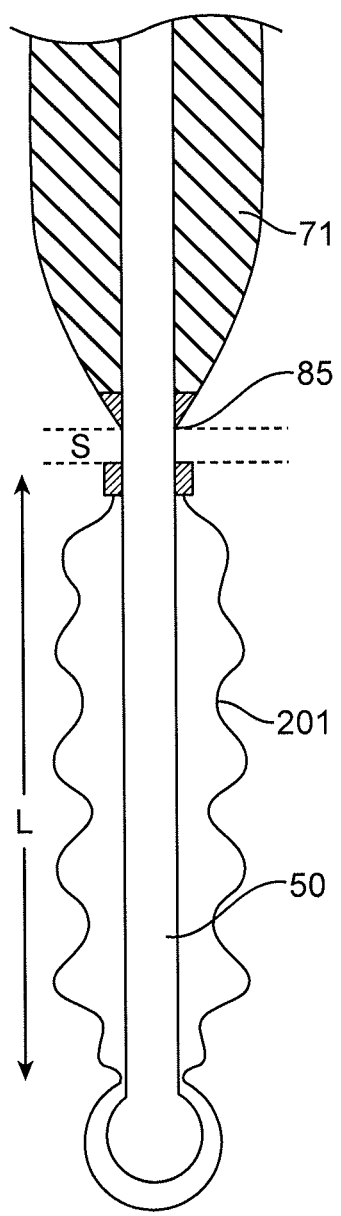
FIG. 55 shows the spacing between a bulking component and a proximal end of the sheath.

Referring to FIG. 7, the proximal portion 30 of the spine 50 can include a bulking component 71. The spine bulking component 71 can increase the diameter of the spine 50 where present. As shown in detail in FIG. 55, the spine bulking component 71 can extend from the distal end of the stem to a distal position 85 along the spine 50 such that a spacing between a distal end of the bulking 71 and the proximal end of the fully extended (unexpanded) sheath 201 is minimized. For example, the spacing s can be 0.25" or less.

Referring to FIGS. 8A-8B, the spine bulking component 71 can be formed of spiral-cut polyethylene terepthalate (PET) tubing. The bulking component 71 can have a 0.095" inner diameter, a 0.125" outer diameter, and a pitch of 0.05". The bulking component 71 can have a tapered distal end to facilitate a smooth transition to the smaller diameter wire of the rest of the spine 50. The spine bulking component 71 can further have a feature at the proximal end that prevents proximal movement by attaching it to the wire joint 1101 (see FIGS. 11-12) of the stem or wire joint sleeve. Further, the spine bulking component 71 can be attached to the wire 82 at one end (such as at a taper) or both ends, thereby preventing movement of the bulking component 71. The spine bulking component 71 can advantageously protect the pylorus from damage due to an increase in surface area with respect to the bare wire 82 (i.e. creating less pressure) and also an "oversized" fit with respect to the wire diameter residing within it (i.e., the diameter of the wire 82 can be much smaller than the inner diameter of the component 71). The difference in diameter can allow the wire 82 to freely move within the component 71, increasing bendability. Further, the spiral-cut helps maintain flexibility without affecting the stiffness of the spine 50.

Figure 9:
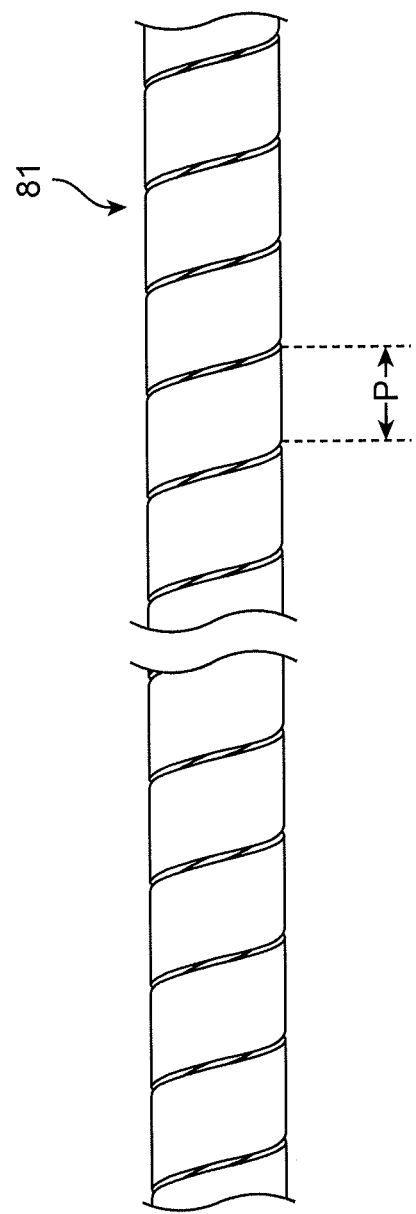
FIG. 9 shows a spiral bulking component of an anchor of a gastrointestinal insert.

Similarly, the anchor 100 can include a bulking component 81. Referring to FIG. 9, the anchor bulking component 81 can be formed of spiral-cut polyethylene terepthalate (PET) tubing. The anchor bulking component 81 can have a 0.045" inner diameter, a 0.065" outer diameter, and a pitch of 0.050". The anchor bulking component 81 can extend over substantially the entire anchor from the pull loop 8377 to the stem 8303.

Further, the anchor bulking component 81 can be attached to the anchor 100 at one or both ends, thereby holding the anchor bulking in place. The anchor bulking component 81 can advantageously protect stomach tissue from damage due to an increase in surface area with respect to the bare wire (i.e. creating less pressure) without affecting the stiffness of the anchor due to the spiral-cut. The spiral-cut also facilitates a smooth outer diameter surface of the anchor by allowing each individual coil to more closely follow the curve of the wire residing within it.

Figure 47:
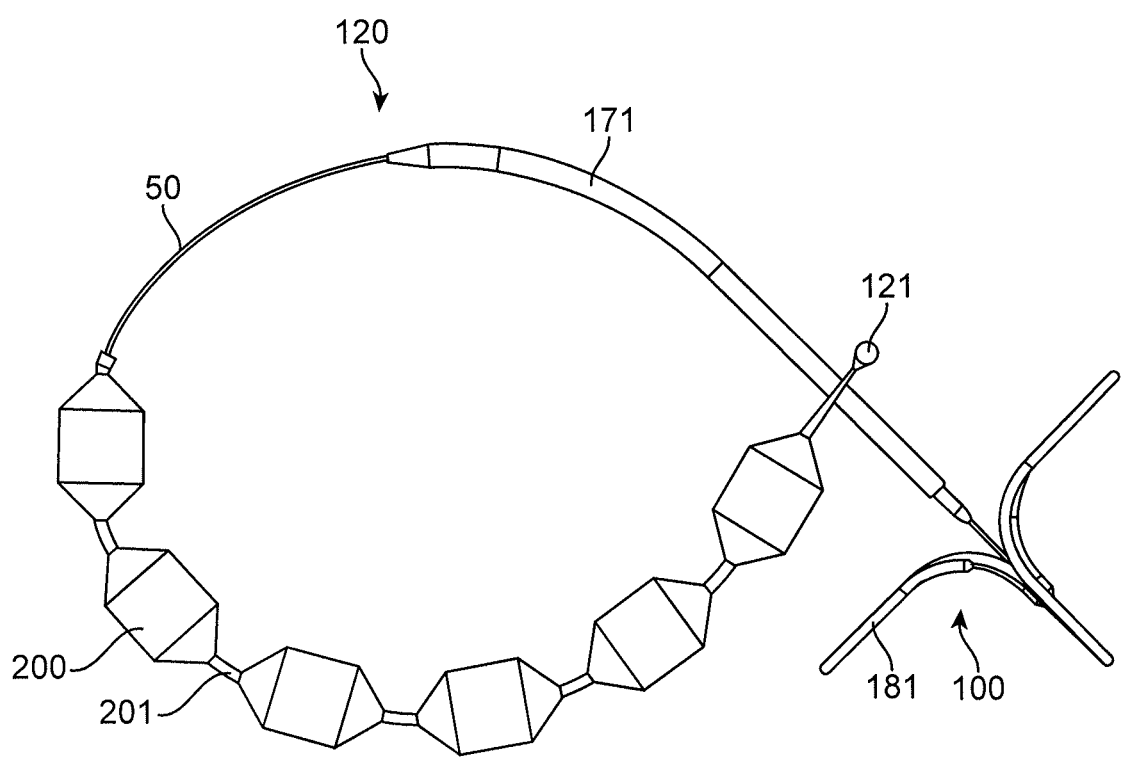
FIG. 47 is a detailed view of the insert of FIG. 2B.

FIG. 47 shows a more detailed view of the insert 120. Like insert 20, the insert 120 includes flow reduction elements 200 that are formed from a sleeve 201 extending along an elongate spine 50 and an anchor 100 in a Figure-8 shape. The insert 120 further includes a straight distal end with an atraumatic ball 121. The end and ball 121 can have an increased or bulked diameter relative to the spine 50 so as to prevent damaging the tissue.

Referring to FIG. 48A, the proximal portion 30 of the spine 50 of insert 120 can include a bulking component 171 similar to bulking component 71, but can include a spiral of higher pitch, such as between 0.05" and 0.25", e.g., 0.125". The pitch can be specifically chosen so as to both avoid the spiral riding up on itself (if the pitch is too low) and avoid losing stiffness (if the pitch is too high). Further, the bulking 171 can have a length of approximately 4 inches. This bulking 171 can be positioned such that the length from a proximal end of the bulking 171 to the distal portion or end 121 of the device is approximately equal to the distance from the pylorus to the fourth portion of the duodenum such that the bulking 171 can be used as a marker during delivery, as described below. Likewise, as described above with respect to FIG. 55, a distal end of the bulking 171 can be positioned such that the spacing between the distal end and the proximal end of the fully extended (unexpanded) sheath 201 is minimized.

Similarly, referring to FIGS. 48A and 48B, the anchor 100 can include a bulking component 181. The bulking component 181 can be similar to bulking component 81, but can include a spiral of higher pitch, such as between 05" and 0.25", e.g., 0.125". Further, the bulking component 181 can cover less of the anchor 100, e.g., so as to cover only about ⅔ of the arch/counterarch area. Covering ⅔ of the anchor can provide sufficient coverage of the wire to prevent damaging the tissue while keeping the pull loop uncovered (to ease grasping) and ensuring that little additional diameter is added to the stem (which can otherwise cause flaring of the arches).

Another exemplary mechanism for bulking the spine or anchor of inserts 20, 120 is shown in FIGS. 10A-10B. There, a thin coating 111, such as of polymer, is applied to the wire of the spine (a similar coating could be placed on the anchor). Yet another mechanism for bulking the spine or anchor is shown in FIG. 10C. There, a thicker (or swollen) wire 113 is used to increase the overall diameter of the anchor of the insert. A similar swollen portion could be placed along the wire of the spine.

Figure 49:
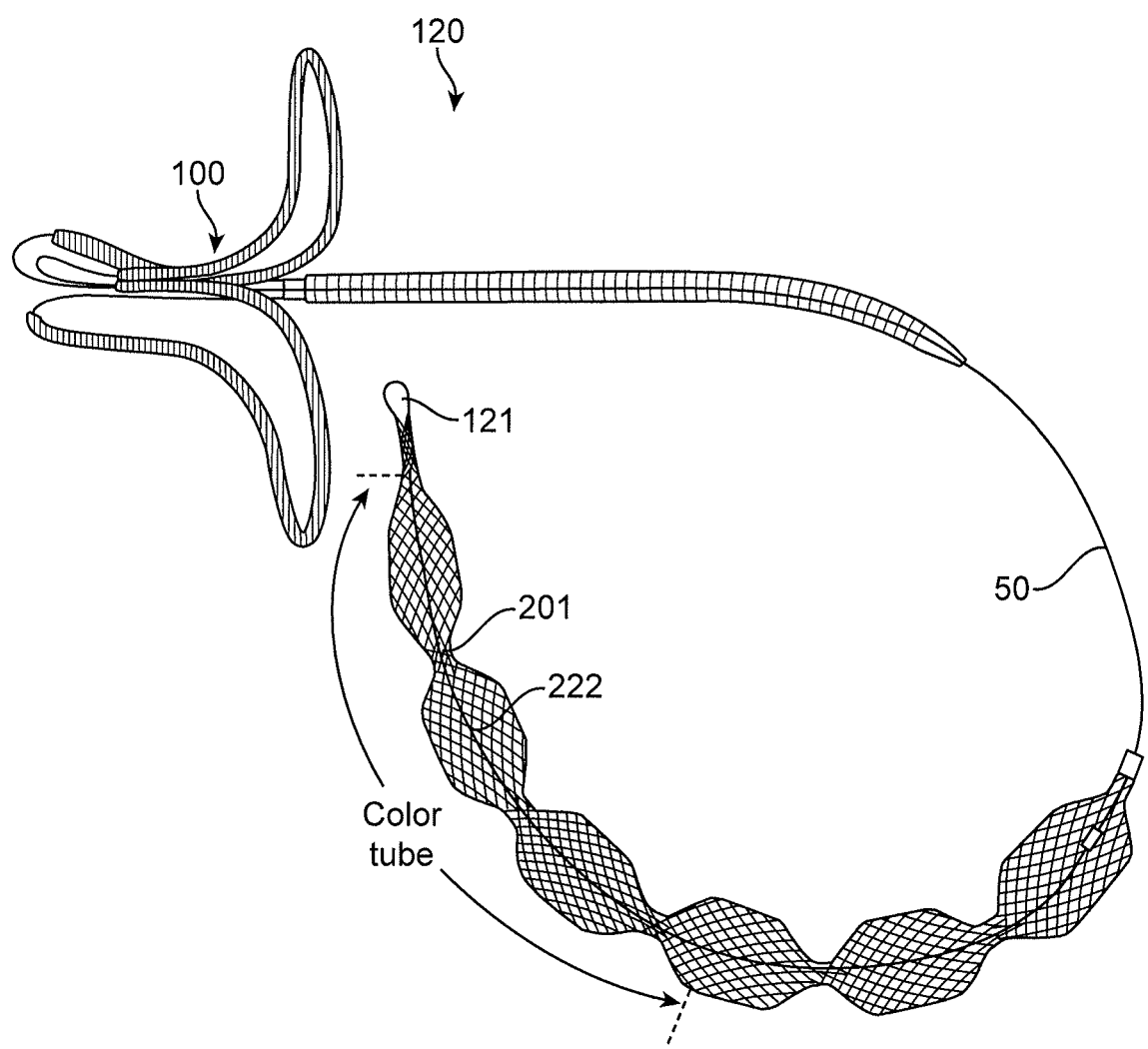
FIG. 49 shows a marker of the insert of FIG. 2B.

Referring to FIG. 49, the insert 120 (or insert 20) can further include one or more markers configured to help with placement of the insert into the gastrointestinal tract. Thus, as shown in FIG. 49, a marker 222 can extend underneath the sheath 201. The marker 222 can be, for example, a colored or textured tube over the wire of the spine 50. The length of the marker 222 can correspond to a desired release location in the gastrointestinal tract. For example, the marker 222 can be about 8 cm long. A proximal end of the marker 222 can be a distance away from the distal end 121 so as to correspond to the distance from the fourth portion of the duodenum to the third portion of the duodenum, as described further below.

Figure 5A:
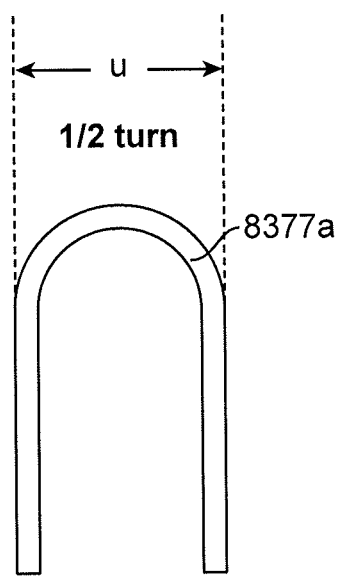
FIG. 5A shows a pull loop of a gastrointestinal insert having a ½ turn.
Figure 5B:
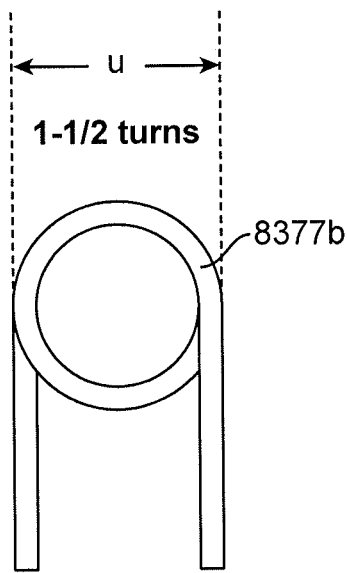
FIG. 5B shows a pull loop having 1½ turns.

Referring to FIGS. 5A-5B, the pull loop 8377 used for insert 20 or 120 can include ½ turn (8377*a*) or more than ½ of a turn (8377*b*), such as ½ turns. By having more than ½ turns, the pull loop 8377*a* can act as a torsion spring to provide increased flexibility to the anchor 100 in a radial direction without substantially decreasing the pull-out strength. Increased radial flexibility (the ability of the pull loop to spread apart when pushed from above) can help minimize tissue interaction as the stomach contracts from a proximal to distal direction. Having more than ½ turns can also increase the durability of the pull loop, allowing torque to be placed on the pull loop, such as during delivery and retrieval, to spread out along a greater distance. The pull loop 8377 can have a diameter u of between 0.10 and 0.20 inches, such as 0.14 inches.

Figures 6A, 6B:
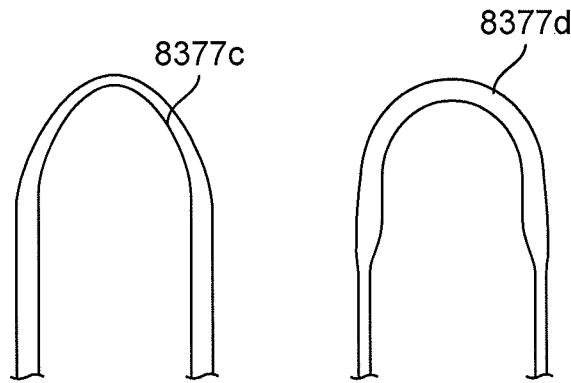
FIGS. 6A-6B show additional variations of pull loops.

Referring to FIGS. 6A-6B, the pull loop 8377 for insert 20 or 120 can likewise include a thinned portion at the proximal end (8377*c*) to increase flexibility or a thickened portion at the proximal end (8377*d*) to increase strength. For example, the wire can be thinned from 0.035 inches to 0.018 inches in pull loop 8377*c* or thickened from 0.035 inches to 0.042 inches in pull loop 8377*d*.

The anchor 100 can have an overall diameter such that, when placed in the stomach perpendicular to the pylorus, the anchor 100 is not able to pass through the pylorus. For example, the anchor 100 can have a diameter of between 2.5 inches and 3.5 inches, such as approximately 3 inches. The proximal anchor 100 is thus adapted and configured to— once delivered through an endoscope and deployed into the stomach—expand to provide a large enough structure that will prevent passage of the anchor through the pylorus.

In some embodiments, the wire used to create the spine can include nubs and/or grooves therein specifically placed to facilitate adhesion with other elements. For example, referring to FIG. 51, the wire 82 used to form the insert 20 (or 120) can include a nub 5101 of increased diameter at the distal end thereof to facilitate adhesion of the distal ball 121 (see FIG. 51A). Further, the wire 82 can include a groove 5103*a* designed to facilitate adhesion of the distal end of the sleeve 201 (see FIG. 51B). Likewise, the wire 82 can include a groove 5103*b* designed to facilitate adhesion of the stopper 59 (see FIG. 51C). The wire 82 can also include a groove 5103*c* designed to facilitate adhesion of the distal end of the spine bulking component 71 (see FIG. 51D). In some embodiments, additional grooves can be used for attachment of the proximal end of the spine bulking and/or one or both ends of the anchor bulking. The nubs and grooves can provide a change in diameter of 0.001" to 0.002", such as 0.0015 inches, which can give an adhesive or glue a circumferential area with which to bond or set, thereby better securing features, such as the ball, sleeve, stopper, and bulking to the wire 82.

Advantageously, the inserts 20, 120 having the features described herein can have a flexible design with respect to radial compression, axial compression, and bending due to the torsion spring design pull loop, the small flexible wire diameter, the FIG. 8 design, the spiral-cut bulking components, and/or the distance from the wire joint to the arches. This flexibility can prevent or reduce tissue interaction when the insert 20 is in place. Simultaneously, the insert 20, due to the Figure-8 design of the anchor 100, can have a high pull-out strength (i.e., resistance to passage through the pylorus), such as greater than 3.5 lb, e.g., approximately 3.8 lb.

The inserts 20, 120 can be delivered by straightening the anchor and pulling or pushing it with a tool directly into the esophagus, into a working channel of an endoscope, or into an overtube.

An exemplary delivery system for an endolumenal device, such as inserts 20, 120 is shown in FIGS. 13-18. The delivery system can include a loading tool 1300, an introducer 1700, and an adaptor 1400 configured to interconnect with one another and with an endoscope.

FIGS. 13A-13D show the loading tool 1300 of the delivery system. The loading tool 1300 includes a hollow elongate body 1301 through which the insert 20 is configured to fit and a connector 1331 at the distal end thereof. The connector 1331 includes a central extension 1333 through which the distal end of the tubular member 1301 extends. The connector 1331 further includes mating arms 1303a,b extend distally from an outer perimeter of the connector 1331. Finally, pins 1317a,b extend distally from the connector 1331. The pins 1317a, b can be offset from one another and thus sit on opposite sides of the central axis 1337 (see FIG. 13B). The elongate body 1301 can have an inner diameter of approximately 0.1 to 0.2 inches, such as approximately 0.148 inches, so as to be able to deliver endolumenal devices that are designed to fit within a working channel of an endoscope, such as a working channel that is 3.7 mm in diameter.

Figure 17:
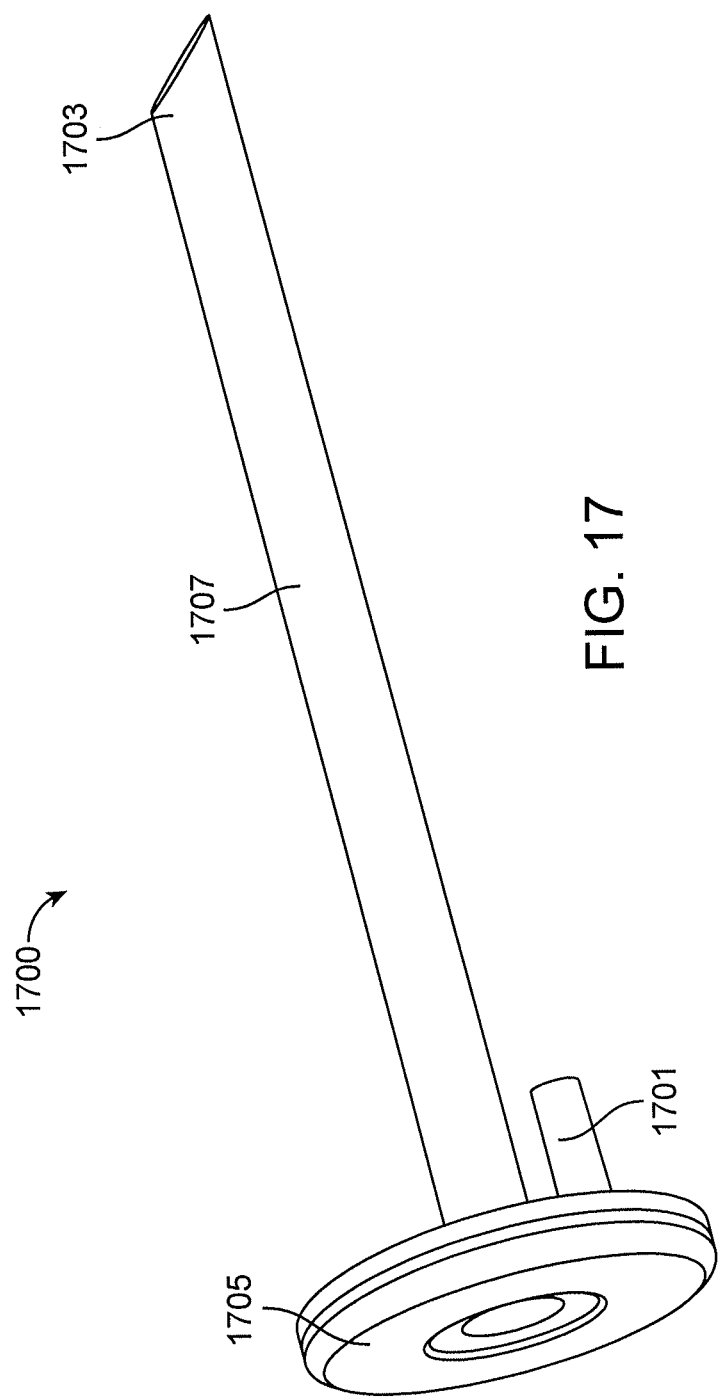
FIG. 17 shows an introducer of an endolumenal delivery system.

FIG. 17 shows the introducer 1700 of the delivery system. The introducer 1700 has a hub 1705 that acts as a stop when placing it into the delivery system and a shaft 1707 extending therefrom. Referring to FIG. 46, the shaft 1701 is configured to extend through the lumen 4609 of the working channel flange 4607 of an endoscope 4600. The shaft 1707 length can be chosen so as to promote advancement of the endolumenal device through the shaft 1707 and down the endoscope 4600 working channel 4605 (instead of backwards out the proximal end 4601 of the endoscope). Accordingly, the shaft 1707 can be sized to end just short of the backside of the working channel 4605. For example, the shaft 1707 can have a length of approximately 2.75 in. Further, the distal shaft tip 1703 can be trimmed at an angle, such as an angle of approximately 45 degrees.

Referring back to FIG. 17, a pin 1701 can extend distally from the hub 1705. Referring again to FIG. 46, the pin 1701 can be positioned such that, upon interaction with the adaptor 1400, the angled tip 1703 extends such that the long end faces the proximal end 4601 of the handle of the endoscope 4600 while the open short end faces the distal end 4603 of the endoscope 4600. This orientation can help facilitate advancement of the insert or device down the endoscope working channel 4605. The outer diameter of the shaft 1707 can be sized to be as large as possible while still fitting into the lumen 4609 of the working channel flange 4607, and the inner diameter of the shaft 1707 can be sized to match the diameter of the working channel 4605. Advantageously, the straight shaft 1707 of the introducer 1700 can help deliver the an endolumenal device through the lumen 4609, which varies in diameter and sizing and can otherwise cause a device to become hung up during delivery.

FIGS. 14A-16B show first and second mating parts 1401a,b of an adaptor 1400. The parts 1401a,b are configured to snap together onto the endoscope handle 4601 and around the working channel flange 4607 (see FIG. 46) on the handle of the endoscope 4600 using tabs 1411a,b. Interlocking features or nubs 1409a-c on one mating part 1401a,b can be configured to interlock with corresponding features on the opposite mating part 1401a,b. When snapped together, the adaptor 1400 includes a bore 1405a configured to allow the shaft 1707 of the introducer 1700 to pass therethrough. When snapped together, the adaptor 1400 further includes a bore 1405b configured to mate with the pin 1701 of the introducer 1700. This mating can not only hold the position of the introducer 1700 in place relative to the endoscope handle, but can lock the mating parts 1401a,b together (by extending the pin 1701 through nub 1409b). When snapped together, the adaptor 1400 further includes tracks 1421a,b configured to mate with arms 1303a,b of the loading tool 1300. Likewise, when snapped together, the adaptor 1400 includes bores 1413a,b configured to mate with pins 1317a,b on the loading tool 1300. This mating can not only hold the position of the locking tube 1300 in place, but can lock the mating parts 1401a,b together (by extending the pins 1317a,b through the nubs 1409a,c).

Figure 18A:
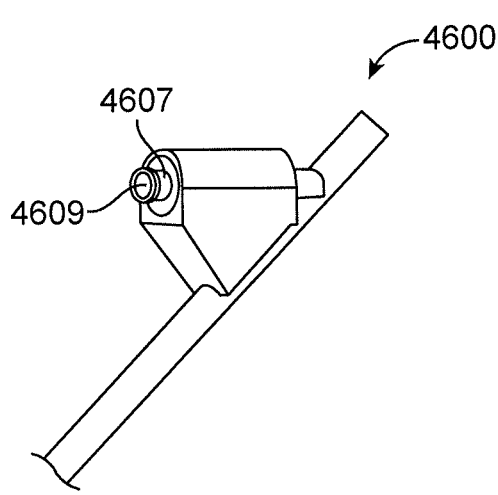
FIGS. 18A-18D show the interconnection of the loading tool of FIGS. 13A-13D, introducer of FIG. 17, adaptor of FIGS. 16A-16B, and endoscope.
Figure 18B:
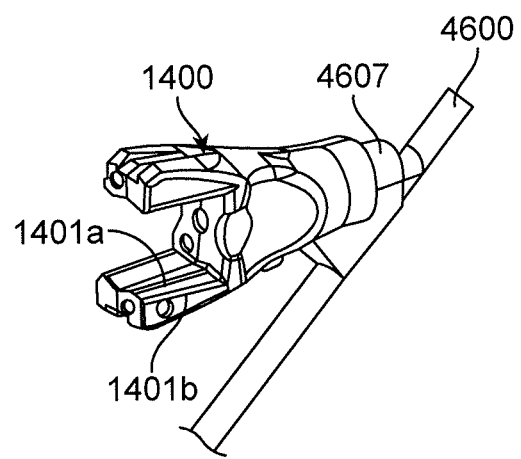
Figure 18C:
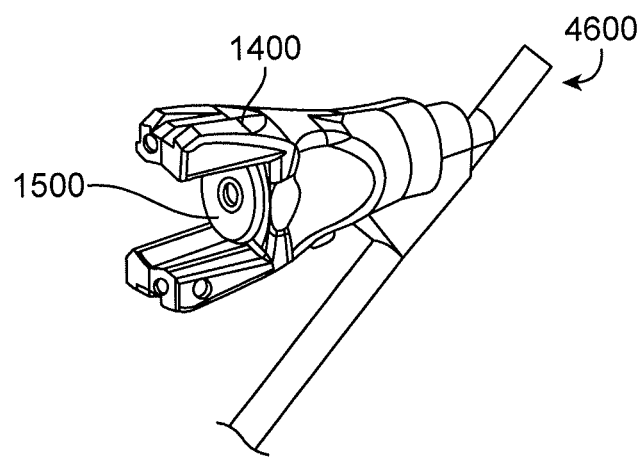
Figure 18D:
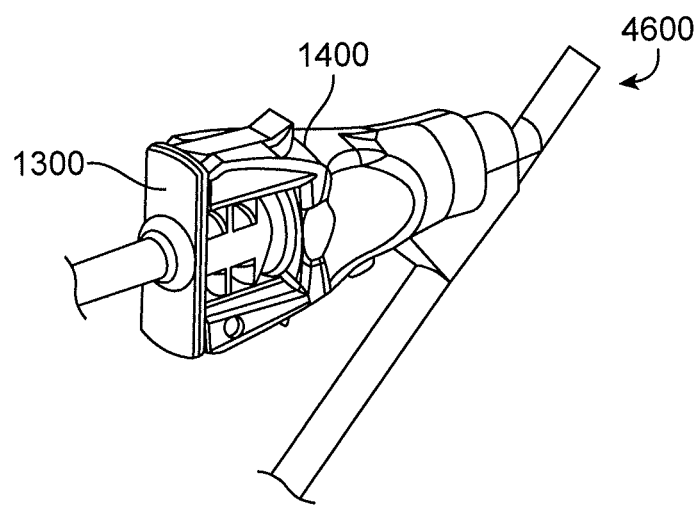

The interconnection of the elements of the delivery system is shown in FIGS. 18A-D. Referring to FIG. 18A, a gasket is remove from the lumen of the working channel flange 4607 (located on the handle of the endoscope 4600). Referring to FIG. 18B, the mating parts 1401a,b of the adaptor 1400 are snapped together onto the endoscope handle and around the end of the working channel flange 4607 of the endoscope handle. Referring to FIG. 18C, the introducer 1700 is then placed into the adaptor 1400 such that the shaft 1707 extends down the length of the lumen 4609 of the working channel flange 4607 up to the Y-connection (shown in FIG. 46A). Further, the angled tip 1703 extends into the working channel of the endoscope in such a way as to block the insert 20 from curving proximally rather than extending distally down the endoscope working channel (shown in FIG. 46). Finally, the loading tool 1300 can be mated with the adaptor 1400 to provide a stable and well aligned path for the insert 20 as it is advanced into the endoscope handle. The interlocking of the loading tool 1300, adaptor 1400, and introducer 1700 with the endoscope 4600 can provide robust connections to one another and to the scope. This robust connection can advantageously counteract the leverage that a user, e.g. a physician, can impart on the delivery system during delivery.

Figure 52A:
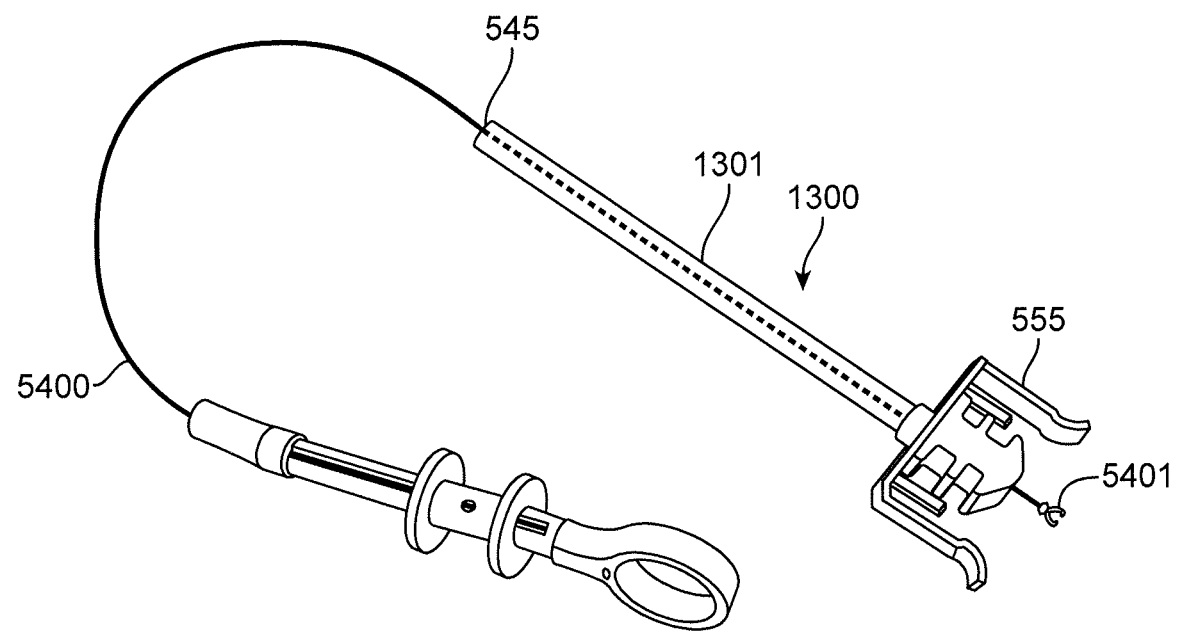
FIGS. 52A-52F show step-by-step loading of an endolumenal device into the loading tool of FIGS. 13A-13D.
Figure 52B:
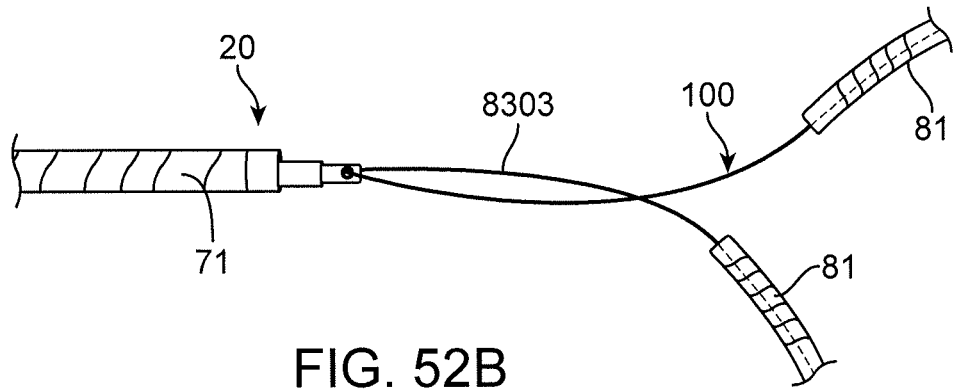
Figure 52C:
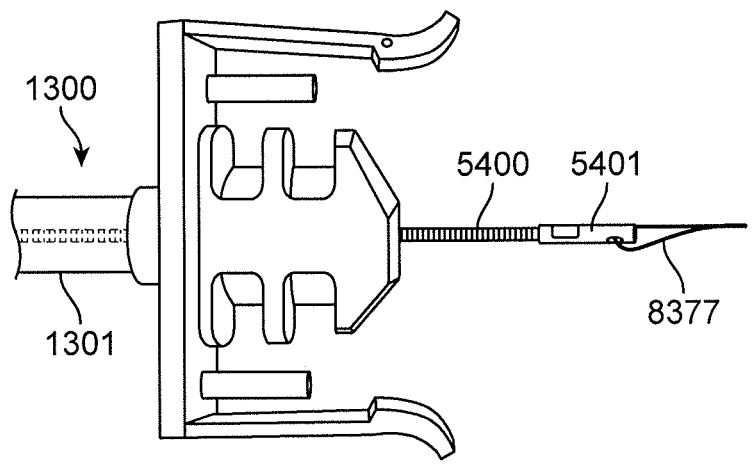
Figure 52D:
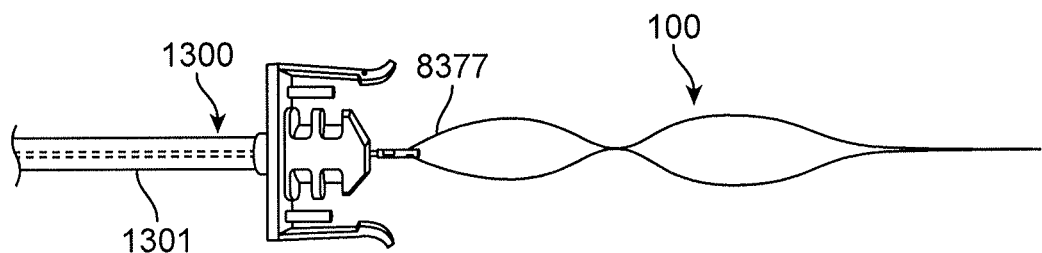
Figure 52E:
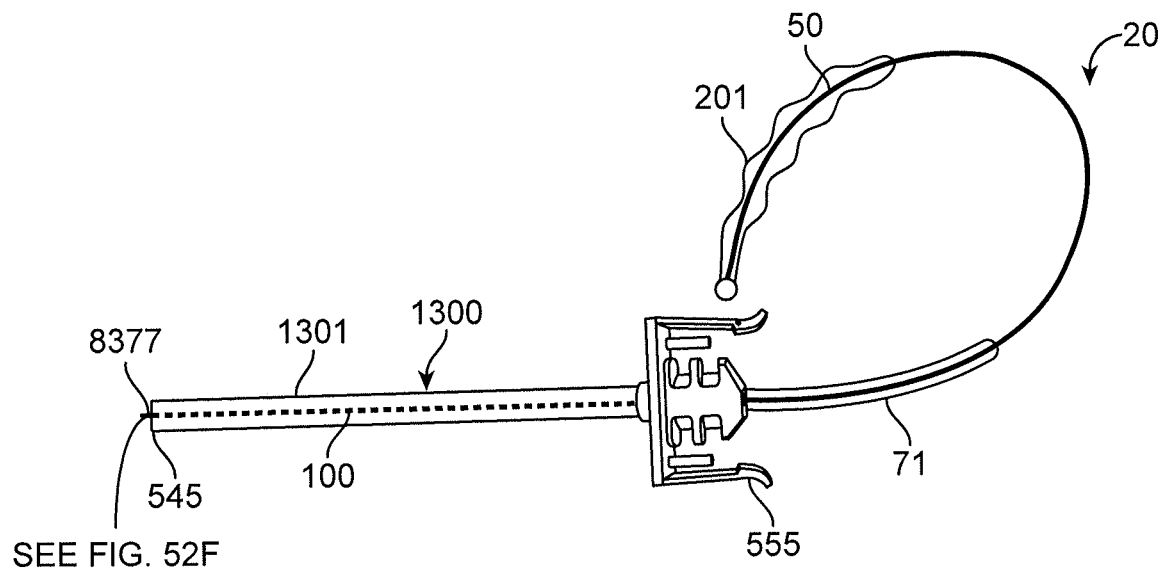
Figure 52F:
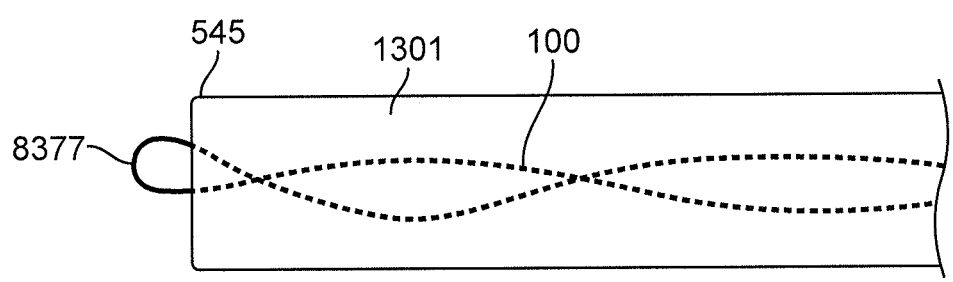

Referring to FIGS. 52A-52F, an insert, such as insert 20 (or 120) can be loaded into the delivery system. As shown in FIG. 52A, a grasper 5400 can first be loaded into the shaft 1301 of the delivery tool 1300 from the proximal end 545 of the tool to the distal end 555 of the tool. The grasper 5400 can be positioned such that the grasping portion 5401 extends out the distal end 555 of the delivery tool 1300. Further, as shown in FIGS. 52B and 52C, the pull loop 8377 can be pulled away from the spine of the insert 20 such that the grasping portion 5401 can grasp the pull loop 8377. As shown in FIG. 52D, the anchor 100 can then be gently stretched so as to straighten or unravel the arches and counterarches. Referring to FIGS. 52E and 52F, the loading tool 1300 can then be pulled over the stretched anchor 100 until the anchor 100 is completely inside the shaft 1301 and the pull loop 8377 extends outside of the proximal end 545 of the shaft 1301, such as by a distance of less than about 5 mm. The spine 50 and distal end of the insert 20 remains primarily outside of the distal end 555 of the loading tool, as shown in FIG. 54E. The insert 20 is then ready to be loaded into the endoscope.

Figure 53A:
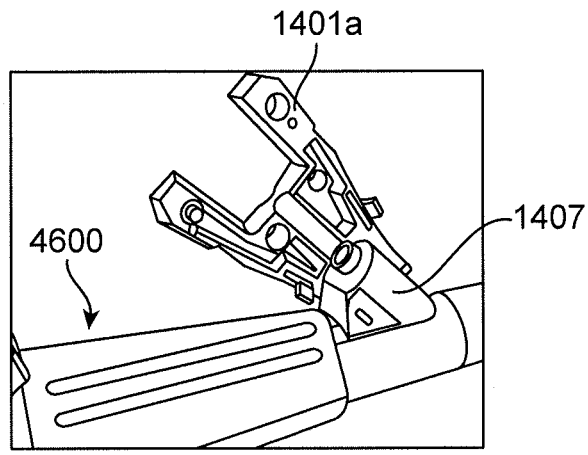
FIGS. 53A-53E show step-by-step connection of adaptor to endoscope, inserter to adaptor, and loading tool to adaptor for the system of FIGS. 18A-18D.
Figure 53B:
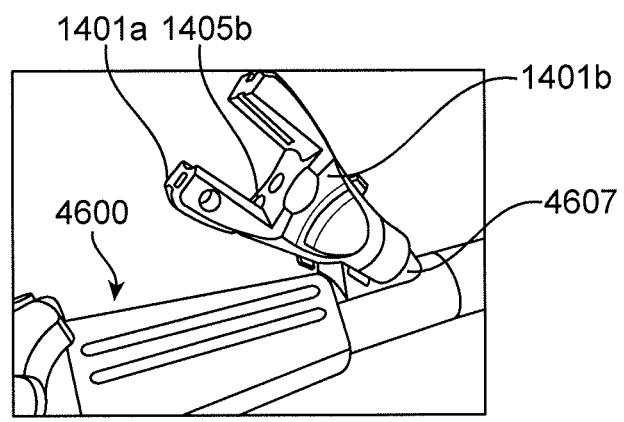
Figure 53C:
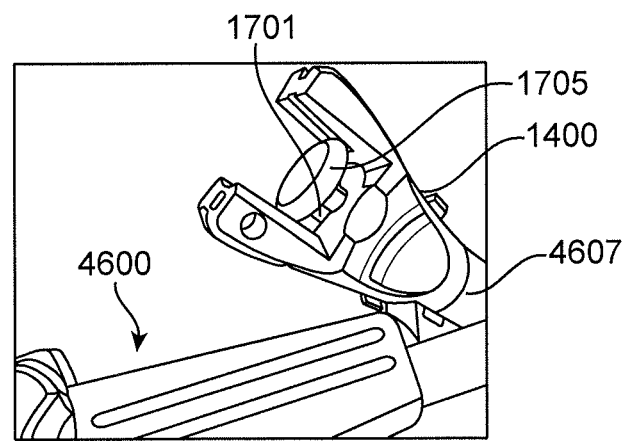
Figure 53D:
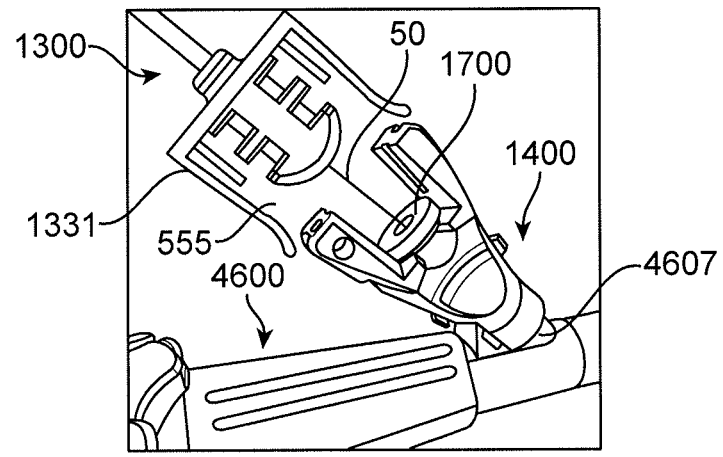
Figure 53E:
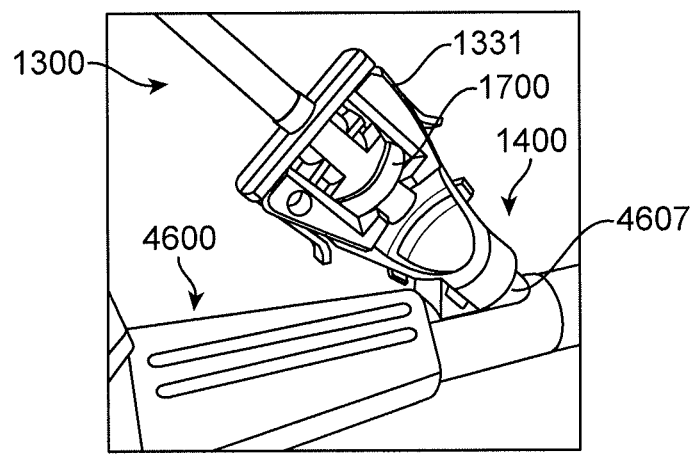

Referring to FIGS. 53A-53E, the endoscope can then be prepared for delivery. To begin, and as shown in FIG. 53A, one part 1401a of the adaptor 1400 can be placed onto the working channel flange 4607. As shown in FIG. 53B, the second part 1401b can then be placed on the opposed side of the working channel flange 4607 and snapped together with the first part 1401a. Referring to FIG. 53C, the introducer 1700 can then be placed into the adaptor 1401 by aligning the pin 1701 with the mating bore 1405*b*. The introducer 1707 can be placed such that the hub 1705 is flush with the adaptor 1400 (and the angled tip extends into the working channel 4605, as shown in FIG. 46A). Referring to FIG. 53D, the spine 50 (extending out of the distal end 555 of the working tool, as shown in FIG. 52E) can then be straightened for delivery into the shaft 1707 of the introducer 1700 (and thus through the lumen 1405*a* of the adaptor 1400). The distal end of the spine 50 can then be loaded into the shaft 1701 of the introducer 1700 while keeping the anchor 100 of the insert 20 still within the loading tool 1300. The sheath 201 can be gently pulled proximally during loading so as to help fit the insert 20 into the shaft 1707. The distal end of the insert 20 can be loaded until the loading tool 1300 can be snapped onto the adaptor 1400 via the connector 1331, as shown in FIG. 53E.

Figure 54:
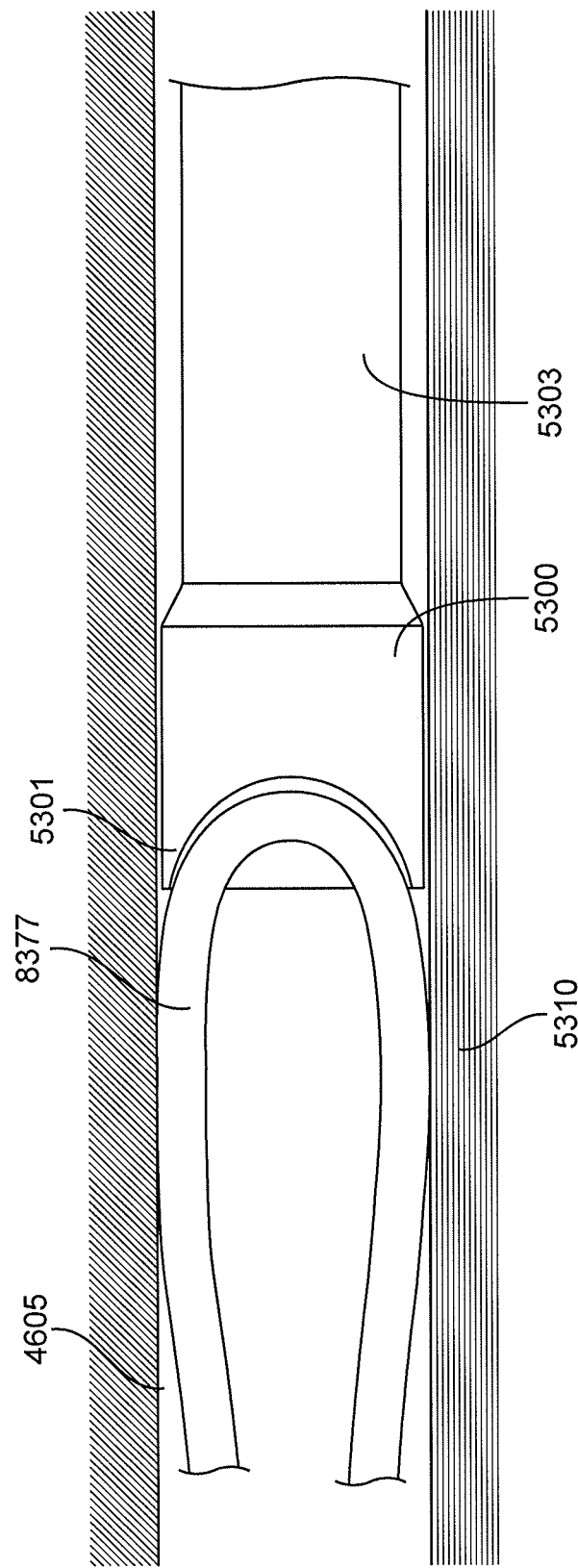
FIG. 54 shows an exemplary pusher inside the working channel of an endoscope.

Referring to FIG. 54, once the loading tool 1300 is snapped onto the adaptor 1400, the pusher 5300 can be used to push the proximal end of the pull loop 8377 through the introducer and into the working channel 4605 of the endoscope for delivery, such as to the small intestine. The loading tool can be removed before pushing the insert all the way down the endoscope.

To place the insert 20 in the small intestine, markers on the insert can be used. For example, the endoscope can be delivered and positioned at the distal tip of the third portion of the duodenum. The insert 20 can then be advanced into the fourth portion of the duodenum by pushing the insert 20 out of the working channel using the pusher 5300. The insert 20 can be advanced until the marker 222 (see FIG. 49) is no longer visible with the endoscope, i.e., such that approximately 10 cm of the insert is out of the endoscope. Once the marker has indicated placement of the distal end of the insert 20 in the fourth portion of the duodenum, the endoscope can be pulled proximally while leaving the insert 20 in the duodenum (i.e., by pushing on the pusher 5300 at the same rate of removal of the scope). Thus, a more proximal portion of the insert 20 is deployed. When the spine bulking 71 is seen, proximal retraction of the endoscope can be stopped, and the endoscope can be used to confirm that the proximal end of the bulking 71 is at the duodenal bulb, just distal to the pylorus. If the proximal end of the bulking 71 is in the second portion of the duodenum, distal of the duodenal bulb, then the endoscope and insert 20 can be retracted together into the bulb. If the proximal end of the bulking 71 is only visible in the stomach, proximal to the pylorus, indicating that the device is too far proximal, then the endoscope and insert 20 may both have to be removed. Assuming that the bulking 71 is in the bulb, endoscope retraction and device advancement can continue until the gastric antrum can be seen. When it is confirmed that the bulking 71 is in the correct place (and extends across the pylorus) from the view within the gastric lumen, the insert can be fully deployed by holding the endoscope in place and advancing the pusher 5300 to pop the anchor 100 into place. Once delivered such that the anchor is in the stomach, the bulking 71 is across the pylorus, and the spine 50 is in the duodenum, the endoscope can be removed.

Figure 50:
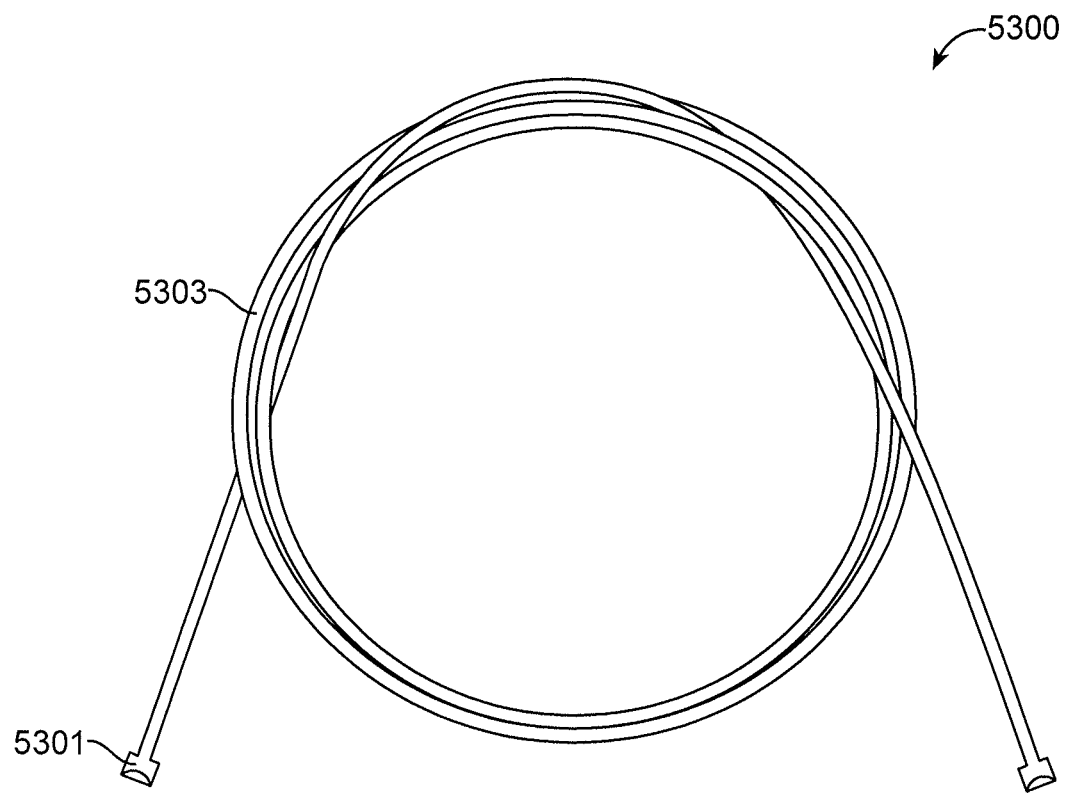
FIG. 50 shows a pusher for use in delivering an endolumenal device out of a working channel of an endoscope.

In some embodiments, the pusher 5300 (shown in FIGS. 50 and 54) can have a distal end 5301 configured to closely match or conform to the proximal end of the pull loop 8377 to maximize engagement with the pull loop 8377. The distal end 5301 can thus have a cupped shape, as further shown in FIG. 50. Moreover, the central length 5303 of the pusher 5300 can have a reduced diameter to increase flexibility and reduce friction within the working channel 4605.

Advantageously, the physician can to deliver the insert 20 using the delivery system described herein with no or minimal additional assistance from other medical technicians, e.g., the insert 20 can be delivered using only a single hand to hold the endoscope and a single hand to deliver the device. Further, the method of delivery described herein can advantageously be used with endoscopes that are rigid or flexible and with gastroscopes or colonoscopes. Further, because the insert can be delivered to the fourth portion of the duodenum without requiring the endoscope to reach the fourth portion of the duodenum, the method can be more easily and successfully performed with a broader range of endoscopes.

Further, the insert 20 can be removed using a removal tube, such as the removal tube 1900 shown in FIGS. 19-20C. The removal tube 1900 can include an elongate member 1901, a hub 1903, and a gasket 1905. The elongate member 1901 can be configured to fit over an endoscope while the gasket 1905 can be configured to seal any space between the endoscope outer diameter and the elongate member 1901 inner diameter to ensure that the stomach remains inflated. Stomach inflation facilitates intra-gastric endoscopic procedures by outwardly displacing tissue to facilitate visualization and minimize tissue damage. Further, the hub 1903 can be sized so as to prevent inadvertent movement of the removal tube down the patient's throat and can include cut-out features 1927*a,b* that allow securement to the patient (such as via tape).

To remove the insert 20 (or 120), the endoscope can be placed into the stomach, and a guidewire delivered. Once the distal tip of the guidewire has exited the scope, the guidewire can be advanced into the stomach until 2-3 coils have been formed inside the stomach (these coils can aid in securing the guidewire). The endoscope can then be removed. The removal tube 1900, with a dilator therein, can be placed together over the guidewire and down the esophagus to the proximal end of the insert. The dilator and guidewire can then be removed, leaving the removal tube 1900 in place. Alternatively, the removal tube 1900 can be placed directly over the endoscope without the use of the guidewire. The stomach can be inflated as needed, using the gasket 1905 to help maintain inflation. Graspers can be extended down the endoscope's working channel. The insert's pull loop or other portion of the anchor 100 can be grabbed with the graspers. Further, the endoscope can be held in place while the graspers are pulled proximally toward the endoscope distal end. The graspers and endoscope can then both be withdrawn into the removal tube until at least the proximal anchor portion of the Insert, such as about 6.5 inches, has been retracted into the removal tube 1900. Once the insert's proximal anchor 100 is inside the removal tube 1900, the endoscope, graspers, and removal tube 1900 can be retracted together.

As described above, the insert described herein can advantageously be flexible enough so as to not substantially irritate, cut, or damage tissue while still providing significant pull-out force to maintain the position of the insert in the gastrointestinal tract. FIGS. 21A-26 show additional features that can be used in conjunction with, or in place with, any of the features described herein to help provide flexibility or floppiness of the spine 50 while maintaining pull-out strength.

Figure 22:
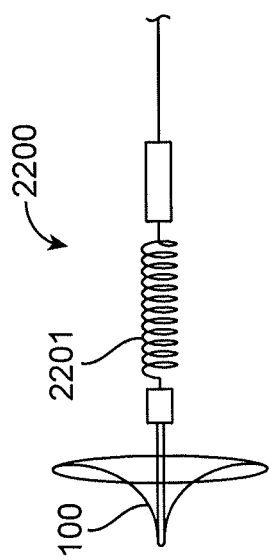
FIG. 22 shows an insert having a tension spring between the anchor and spine.
Figure 21:
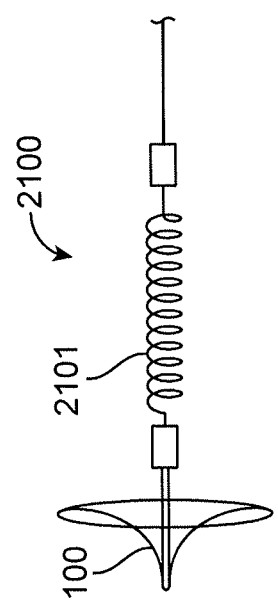
FIG. 21 shows an insert having a compression spring between the anchor and spine.
Figure 23A:
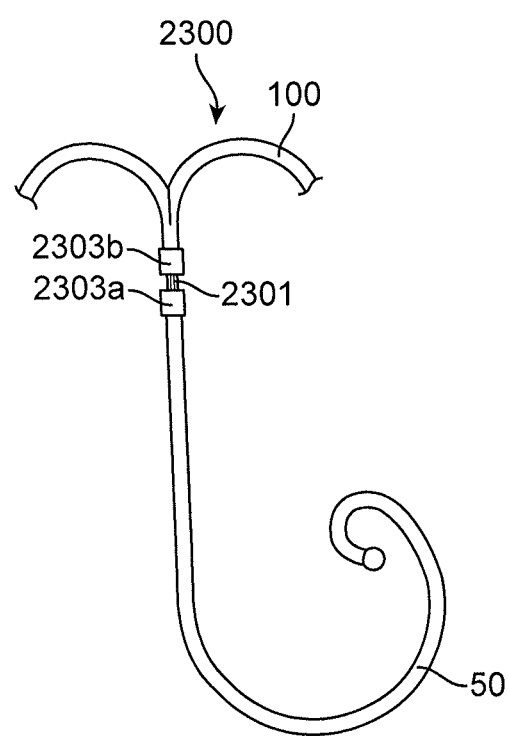
FIGS. 23A-23D show an anchor having multiple wire strands between the anchor and spine.
Figure 23B:
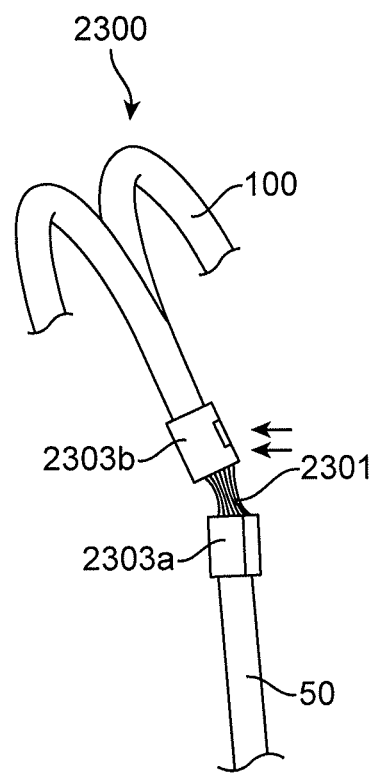
Figure 23C:
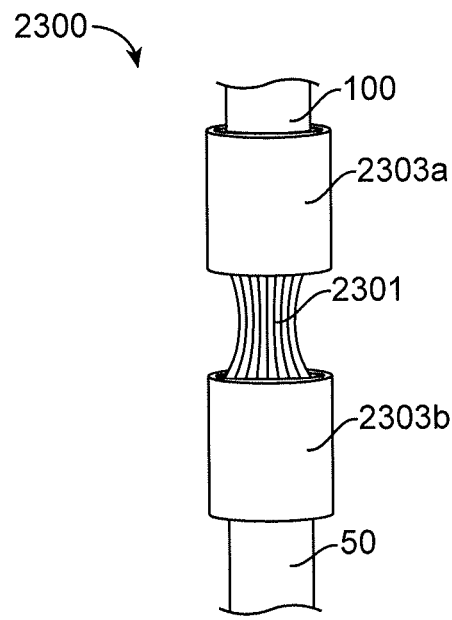
Figure 23D:
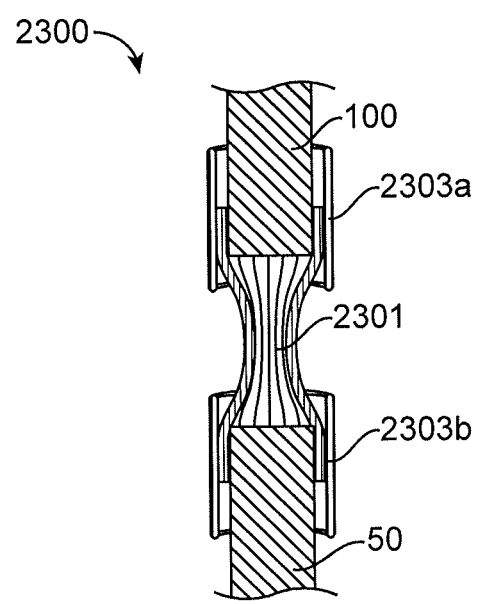

For example, FIG. 21 shows an insert 2100 including a compression spring 2101 just distal to the anchor 100 so as to increase flexibility while maintaining pull-out force. Likewise, FIG. 22 shows an insert 2200 including a tension spring 2201.

FIGS. 23A-23D show a device 2300 including multiple wire strands 2301 extending parallel just distal to the anchor 100. The wire strands 2301 are placed around the circumference and can advantageously provide bending and flexibility between the anchor 100 and the spine 50. Crimps 2303a,b capture the individual wire strands 2301 and connect the strands 2301 to the anchor 100 and spine 50.

Figure 24:
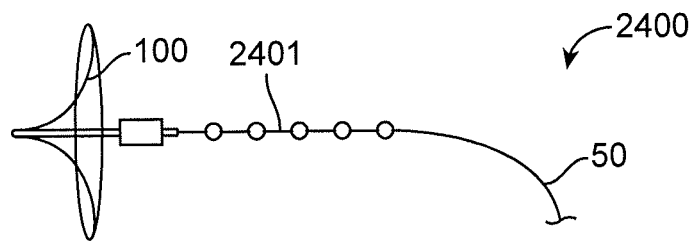
FIG. 24 shows an insert including chain links therein.
Figure 25A:
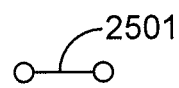
FIGS. 25A-25D show exemplary chain links for the insert of FIG. 24.
Figure 25B:
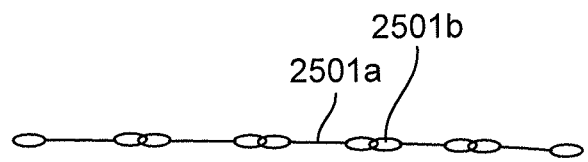
Figure 25C:
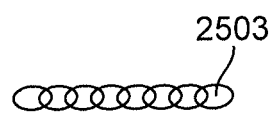
Figure 25D:
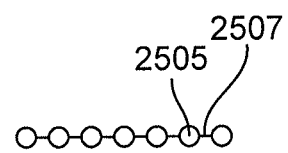

FIG. 24 show an insert 2400 including chain links 2401 between the anchor 100 and spine 50 that can advantageously bend without spring feedback imported to the stomach. The chain links 2401 can transfer compressive linear forces when constrained in a tube. This can be advantageous for loading the insert 2400 through the scope into the stomach and duodenum. The chain can be comprised of one or more links. Exemplary chains and links are shown in FIGS. 25A-25D. FIG. 25A shows a ring and post single link 2501. FIG. 25D shows multiple ring and post links 2501a,b connected together. FIG. 25C shows multiple rings 2503. FIG. 25D shows a ball 2505 and chain 2507 connected together. The ball and chain design of FIG. 25D can have a reduced amount of angulation, which can be advantageous for controlling introduction and placement. It can also swivel freely, allowing the proximal anchor 100 to rotate. The various chain links shown in FIGS. 25A-25D can be connected to the anchor 100 and spine 50 through crimping or other connection mechanisms.

Figure 26:
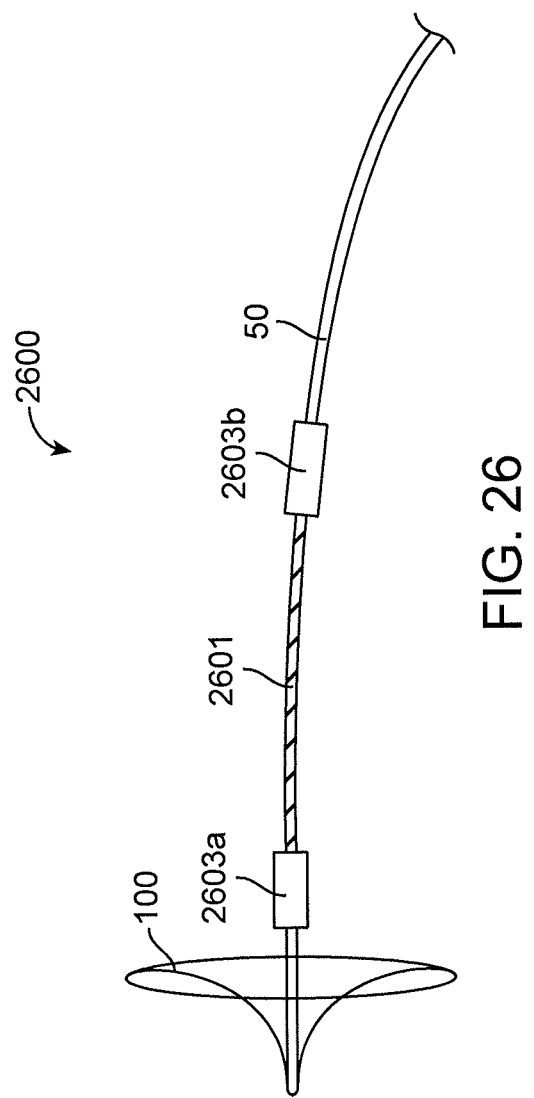
FIG. 26 shows an insert including a cable between the anchor and spine.
Figure 27A:
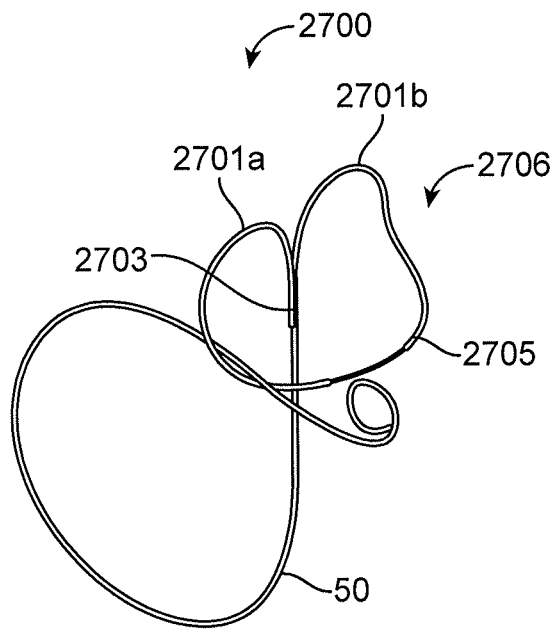
FIGS. 27A-27D show another embodiment of an anchor.
Figure 27B:
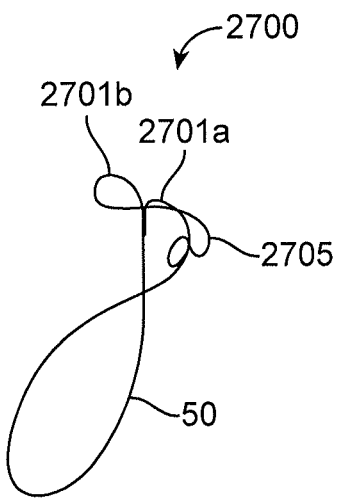
Figure 27C:
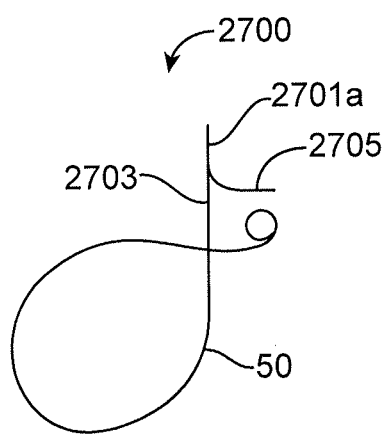
Figure 27D:
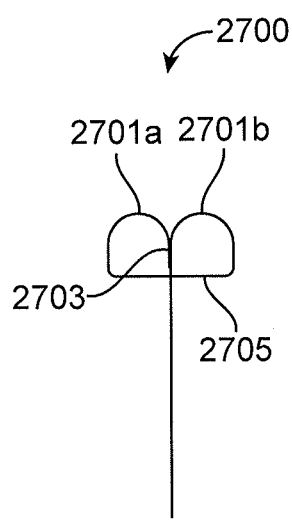
Figure 28A:
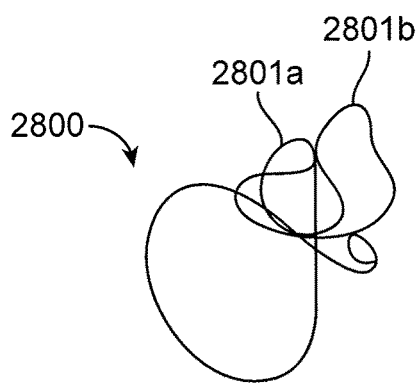
FIGS. 28A-28F show another embodiment of an anchor.
Figure 28B:
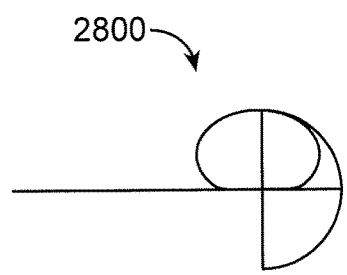
Figure 28C:
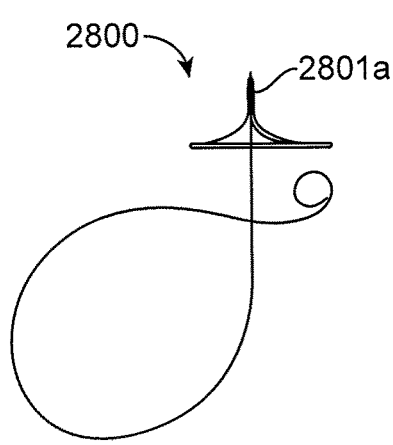
Figure 28D:
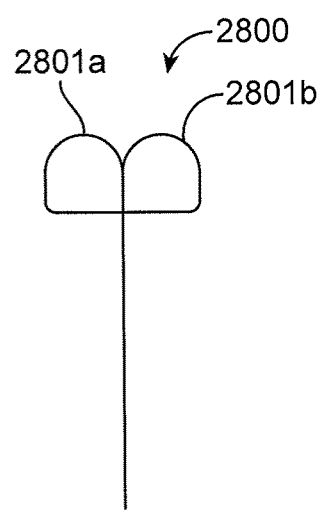
Figure 28E:
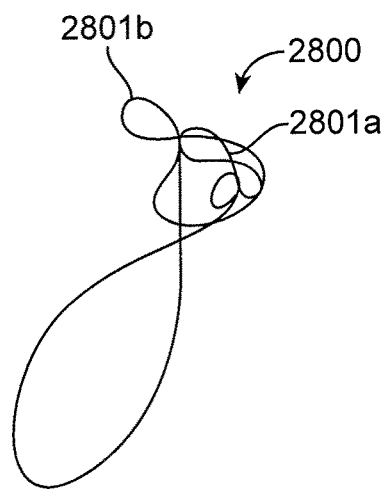
Figure 28F:
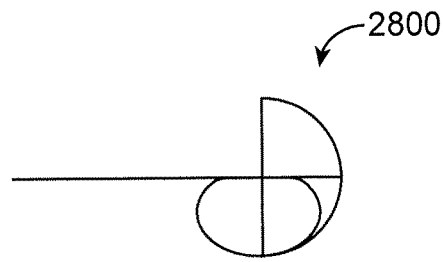

FIG. 26 shows an insert 2600 including a cable 2601 between the anchor 100 and spine 50. The cable 2601 can be connected to the anchor 100 and spine 50 at joints 2603a,b, such as through crimping, and can advantageously provide increased flexibility.

FIGS. 27A-38E show alternative anchor that designs that, alone or in combination with other features described herein, can likewise provide the desired flexibility and pull-out force.

Figure 32A:
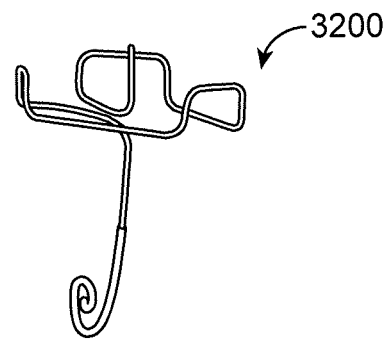
FIGS. 32A-32C show another embodiment of an anchor.
Figure 32B:
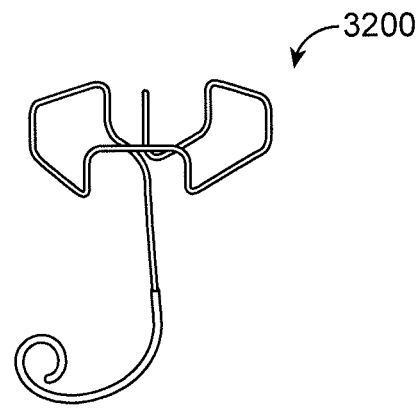
Figure 32C:
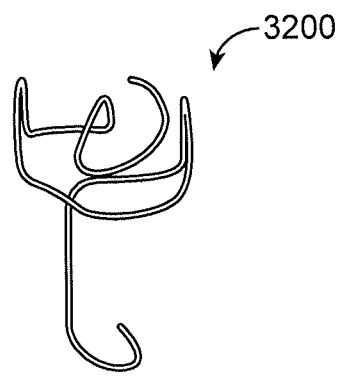

For example, the anchor 2700 of FIGS. 27A-27D includes two arches 2701a,b connected together by a single counter-arch 2705 on one side of the spine 2703. Another exemplary anchor 2800 is shown in FIGS. 28A-28F. The anchor 2800 includes two arches 2801a,b connected together around approximately ¾ of the circumference. FIG. 30 shows an anchor 3000 having a substantially planar Figure-8 formation. The anchor 3000 can include a latch 3001 configured to engage the wires to maintain the shape. A soft bendable pull-section or hinge 3003 can advantageously increase flexibility. FIGS. 31A-31E show an anchor 3100 having a circular base 3103 and a perpendicular pigtail feature 3101. FIGS. 32A-32C show another anchor 3200. Although the wire forming the anchor 3200 is shown as having sharp turns, the anchor 3200 can also have the same shape but with rounded features.

Figure 29:
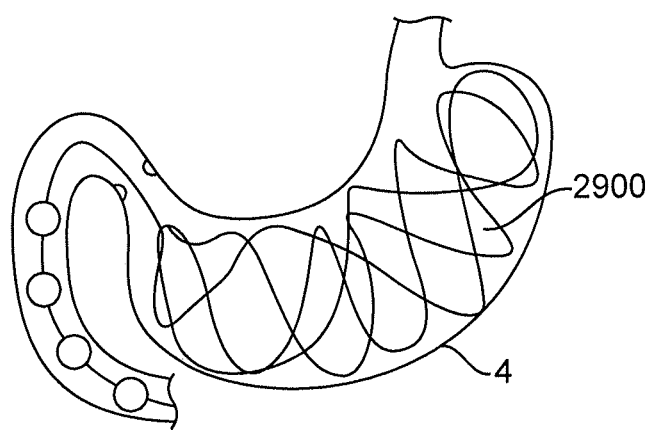
FIG. 29 shows an exemplary braided proximal anchor.
Figure 30A:
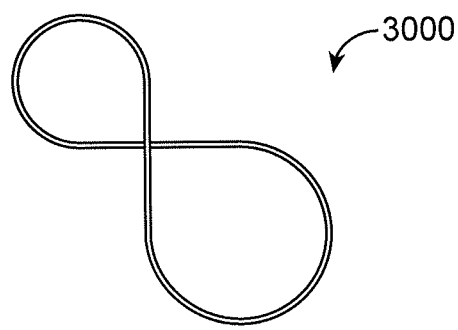
FIGS. 30A-30E show another embodiment of an anchor.
Figure 30B:
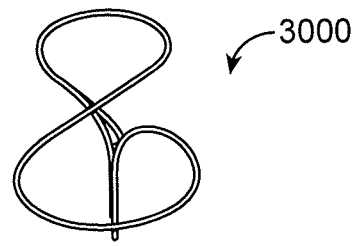
Figure 30C:
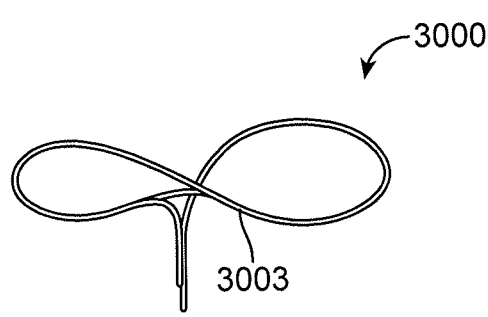
Figure 30D:
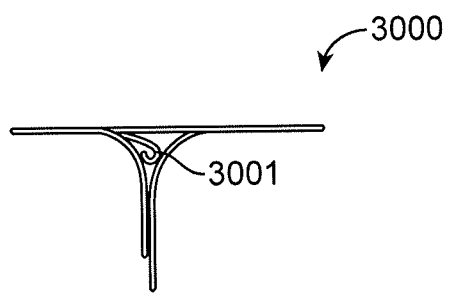
Figure 30E:
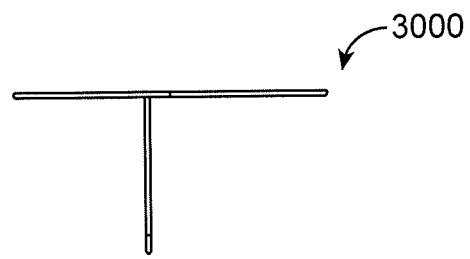
Figure 35:
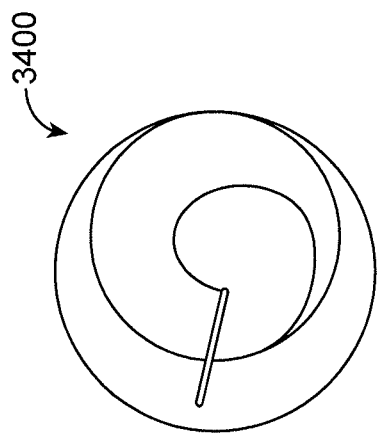
FIGS. 34 and 35 show side and top view of another embodiment of an anchor.
Figure 34:
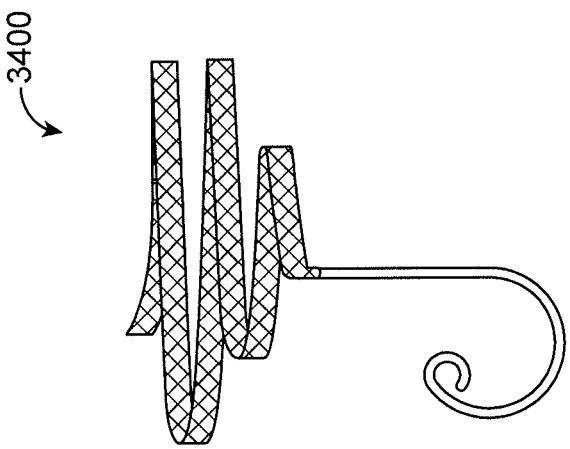
Figure 33:
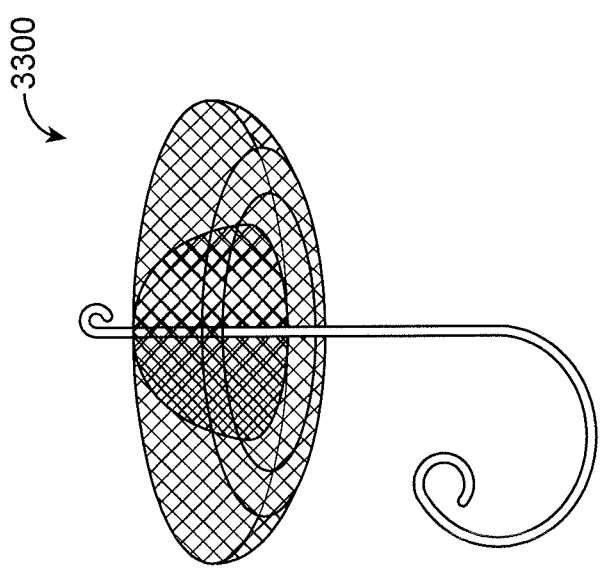
FIG. 33 shows another embodiment of an anchor.

FIG. 29 shows an exemplary braided proximal anchor 2900 in the stomach 4. The anchor 2900 can be constructed as a large braid that behaves similar to a scaffold in the stomach 4. The anchor 2900 can substantially fill the stomach or just a portion of the stomach. FIG. 33 shows an exemplary hat anchor 3300, and FIGS. 34 and 35 shows an exemplary collar anchor 3400. The anchors 3300, 3400 can be made, for example, out of a braided material.

Figure 36A:
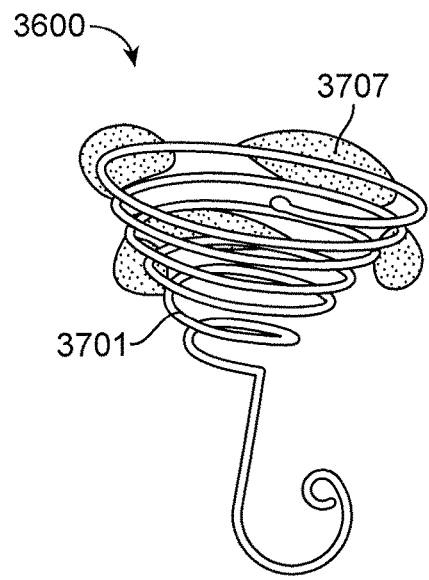
FIGS. 36A-36C show another embodiment of an anchor.
Figure 36B:
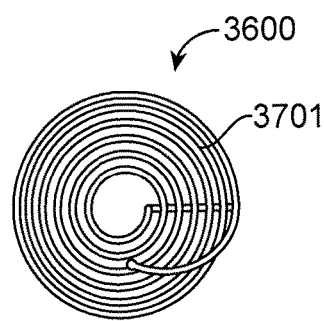
Figure 36C:
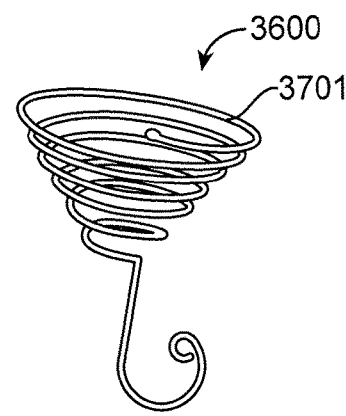
Figure 37A:
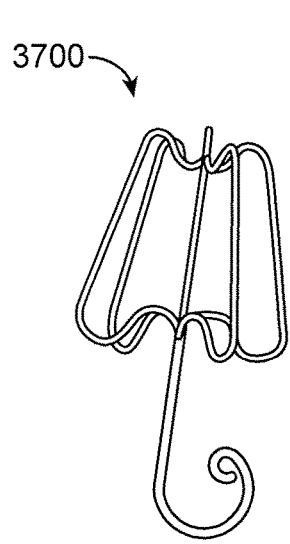
FIGS. 37A-37C show another embodiment of an anchor.
Figure 37B:
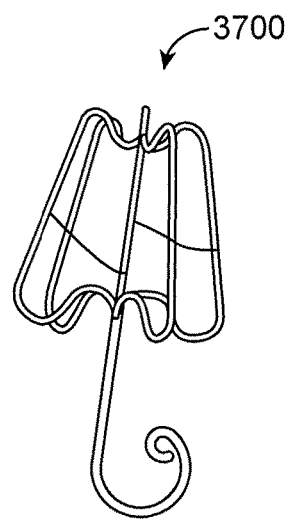
Figure 37C:
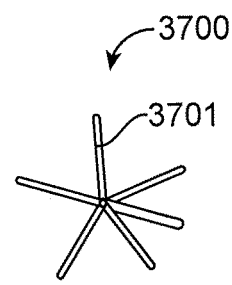

FIGS. 36A-36C show an exemplary anchor 3700 including a spiral wire feature 3701 widening from the distal end to the proximal end. In some embodiments, the anchor 3700 can include a braid 3707 covering some or all of the spiral wire feature 3701. FIGS. 37A-37C show another embodiment of an anchor 3700 having spines 3701 extending in such a way as to resemble a partially collapsed umbrella.

FIGS. 38A-38E show another exemplary anchor 3800 made of a wire formed approximately into the shape of a four-leaf clover.

Figure 39:
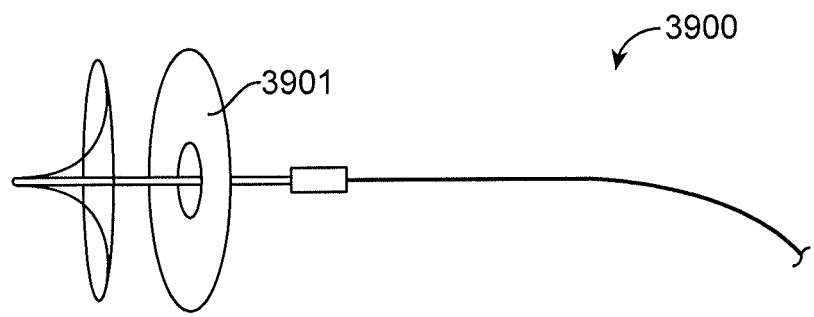
FIG. 39 shows an insert including a washer as a bulking component.
Figure 40:
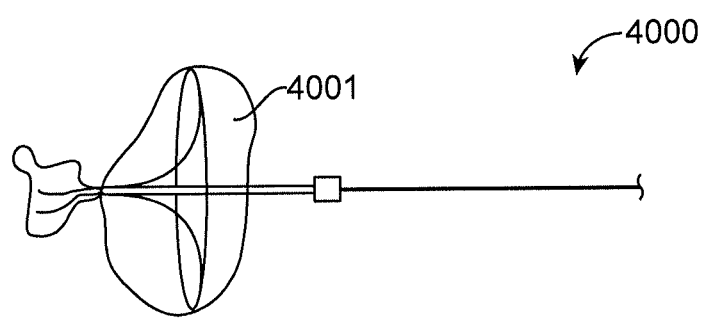
FIG. 40 shows an insert including a cinchable bag as a bulking component.

FIGS. 39 and 40 show alternatives to the bulking components described above. That is, FIG. 39 shows an insert 3900 including a washer 3901 designed to provide bulking to protecting tissue from damage. FIG. 40 shows an insert 4000 including a cinchable bag 4001 that can likewise be used to protect the tissue from damage.

Figure 41B:
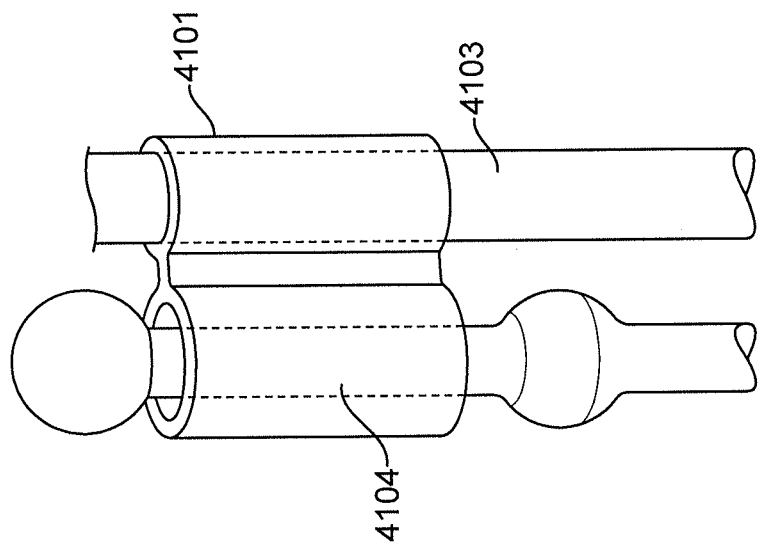
FIG. 41B shows a collar providing flexibility to the anchor of FIG. 41A.
Figure 41A:
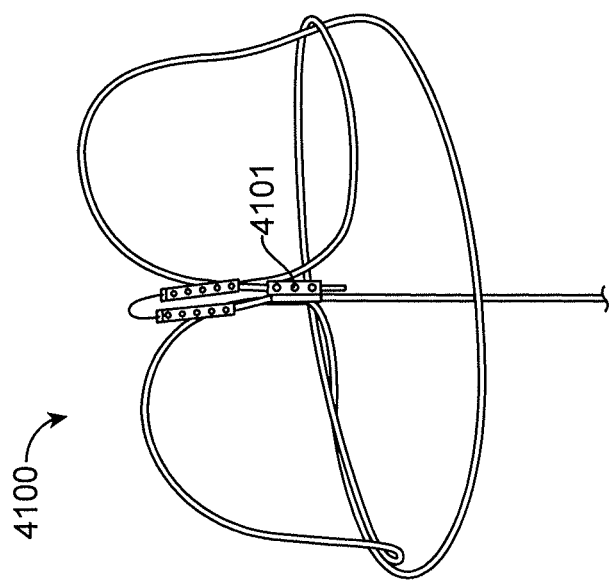
FIG. 41A shows another embodiment of an anchor.

FIGS. 41A and 41B show an alternative anchor 4100 in which the wire joint 4101 is captured axially but otherwise allowed to spin. That is, the collar 4101 can be crimped to one of the wires 4103 while allowing the second wire 4104 to freely rotate therein. This design can advantageously counteract tangling, or twisting of the wires of the anchor, during delivery.

Figure 42:
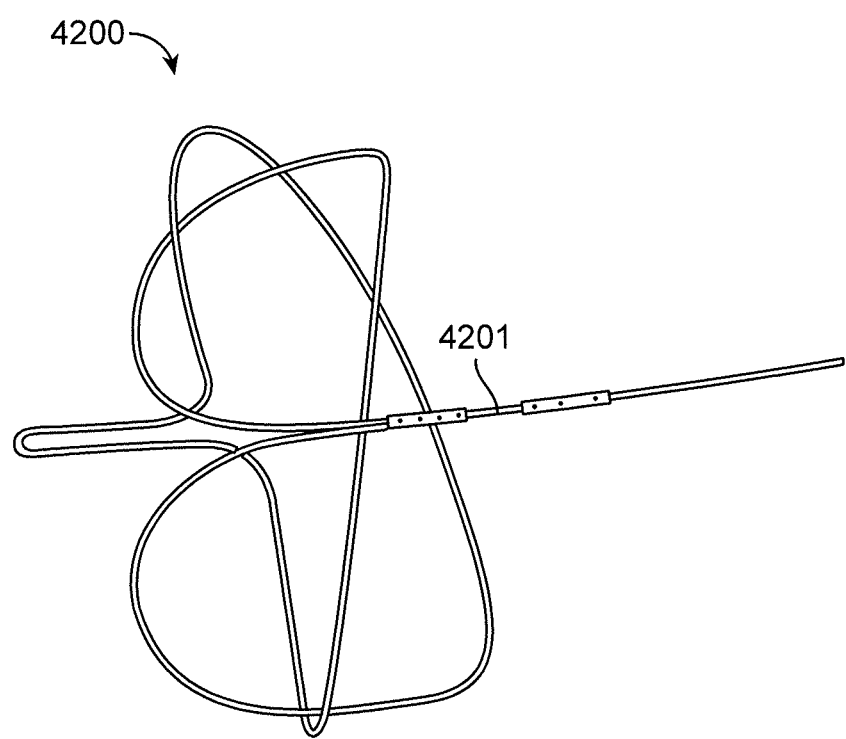
FIG. 42 shows a rotatable anchor.
Figure 43:
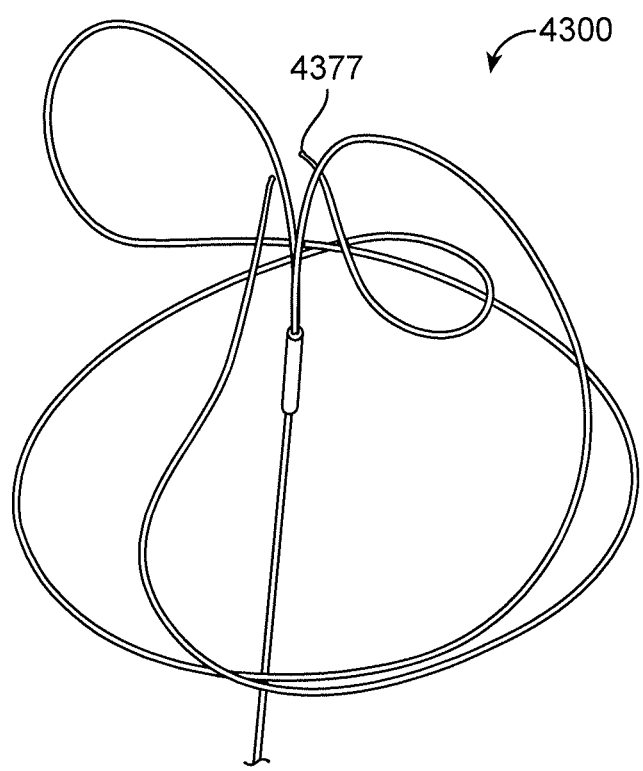
FIG. 43 shows an anchor having a slit pull loop.

FIG. 42 shows an anchor 4201 that is allowed to freely rotate, at rotation element 4201, with respect to the rest of the device, also helping with tangling. Likewise, FIG. 43 shows an anchor 4300 where the pull loop 4377 is split down the center, allowing for more freedom of movement and less tanging.

Figure 44:
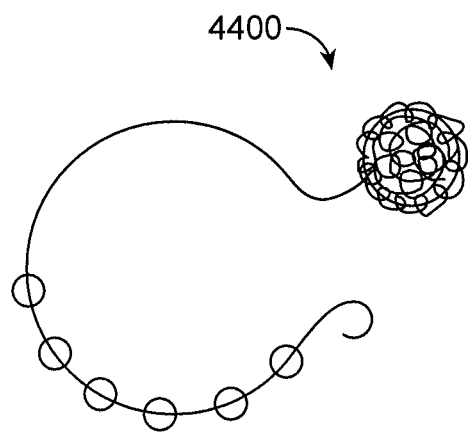
FIG. 44 shows another embodiment of an anchor.
Figure 45:
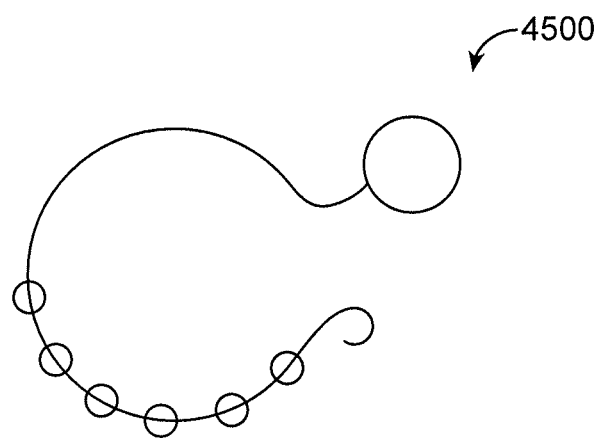
FIG. 45 shows a balloon anchor.

FIG. 44 shows an anchor 4400 formed to look similar to a spherical ball of yarn, and FIG. 45 shows an anchor 4500 formed of a balloon, both of which can advantageously reduce tissue damage.

Any of these anchor designs can be used in conjunction with, or in addition to, the anchors 100 described above with respect to inserts 20, 120.

Unless defined otherwise, all technical terms used herein have the same meanings as commonly understood by one of ordinary skill in the art of gastrointestinal interventional technologies. Specific methods, devices, and materials are described in this application, but any methods and materials similar or equivalent to those described herein can be used in the practice of the present invention. While embodiments of the invention have been described in some detail and by way of exemplary illustrations, such illustration is for purposes of clarity of understanding only, and is not intended to be limiting. Still further, it should be understood that the invention is not limited to the embodiments that have been set forth for purposes of exemplification, but is to be defined only by a fair reading of claims that are appended to the patent application, including the full range of equivalency to which each element thereof is entitled.

What is claimed is:

1. A method of loading an unsheathed endoluminal device into a working channel of an endoscope, comprising:
    attaching an adaptor to a handle of the endoscope such that a channel of the adaptor is in communication with the working channel of the endoscope;
    loading the unsheathed endoluminal device into a lumen of a loading tool from a coupling end of the loading tool to an open end of the loading tool until a proximal end of the device is positioned at the open end;
    connecting the coupling end of the loading tool to the adaptor; and
    pushing the proximal end of the unsheathed endoluminal device distally along the lumen of the loading tool through the adaptor and into the working channel.

2. The method of claim 1, wherein loading the unsheathed device comprises loading such that a distal end of the device remains outside of the loading tool, the method further comprising advancing the distal end of the unsheathed endoluminal device into the channel of the adaptor.

3. The method of claim 1, further comprising removing the loading tool from the adaptor and continuing to push the proximal end of the unsheathed endoluminal device distally until the unsheathed endoluminal device is completely within the working channel.

4. The method of claim 3, wherein pushing the proximal end of the unsheathed endoluminal device comprises pushing until the proximal end of the device is between 0 mm and 5 mm within the channel of the adaptor, and wherein the removing step comprises removing after the pushing step.

5. The method of claim 1, further comprising placing an introducer through the channel of the adaptor such that a portion of the introducer extends into the working channel, wherein pushing the proximal end of the unsheathed endoluminal device distally through the channel of the adaptor comprises pushing the device through a lumen of the introducer.

6. The method of claim 5, wherein the portion of the introducer extending into the working channel is an angled tip.

7. The method of claim 1, wherein loading comprises using graspers to pull on the proximal end of the endoluminal device.

8. The method of claim 1, wherein attaching the adaptor comprises snapping the adaptor around the handle.

9. The method of claim 1, wherein attaching the adaptor to the handle comprises attaching the adaptor and handle such that the adaptor is fixed in position relative to the endoscope.

10. A system for delivering an unsheathed intragastric device through an endoscope, the system comprising:
    a delivery tool having an elongate tube configured to hold a portion of the unsheathed intragastric device therein and a first connector on a distal end of the elongate tube; and
    an adaptor configured to attach to a handle of the endoscope, the adaptor configured to mate with the first connector of the delivery tool, wherein the elongate tube of the delivery tool is configured to align with the channel of the adaptor when the first and second connectors are mated in order for the unsheathed intragastric device to move from the delivery tool into the working channel of the endoscope.

11. The system of claim 10, further comprising an introducer having a tubular member configured to extend through the channel of the adaptor and into the working channel of an endoscope.

12. The system of claim 11, wherein the tubular member has an angled end configured to extend into the working channel.

13. The system of claim 12, wherein the introducer further includes a pin configured to mate with a slot in the adaptor, the pin and slot further configured to orient the angled end within the working channel.

14. The system of claim 10, wherein the adaptor comprises a first mating part and a second mating part, the first and second mating parts configured to snap together around a portion of the endoscope handle.

15. The system of claim 14, wherein the first connector includes a first pin and a second pin and the adaptor includes a first bore in the first mating part and a second bore in the second mating part, the first pin configured to fit within the first bore and the second pin configured to fit within the second bore when the first and second connectors are mated.

16. The system of claim 10, wherein the first and second connectors are snapping features.

* * * * *